US010087236B2

(12) United States Patent
Wong et al.

(10) Patent No.: US 10,087,236 B2
(45) Date of Patent: *Oct. 2, 2018

(54) METHODS FOR MODIFYING HUMAN ANTIBODIES BY GLYCAN ENGINEERING

(75) Inventors: Chi-Huey Wong, La Jolla, CA (US); Chung-Yi Wu, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/959,351

(22) Filed: Dec. 2, 2010

(65) Prior Publication Data

US 2011/0263828 A1   Oct. 27, 2011

Related U.S. Application Data

(60) Provisional application No. 61/265,757, filed on Dec. 2, 2009.

(51) Int. Cl.
*C07K 16/00* (2006.01)
*C12P 21/00* (2006.01)

(52) U.S. Cl.
CPC ............ *C07K 16/00* (2013.01); *C12P 21/005* (2013.01); *C12Y 204/01038* (2013.01); *C12Y 204/99* (2013.01); *C12Y 302/01051* (2013.01); *C07K 2317/10* (2013.01); *C07K 2317/21* (2013.01); *C07K 2317/41* (2013.01)

(58) Field of Classification Search
CPC ............ C12P 21/005; C12Y 204/1038; C12Y 204/99; C12Y 302/1051; C07K 2317/10; C07K 2317/21; C07K 2317/41
USPC ..................................... 424/133.1; 530/387.3
See application file for complete search history.

(56) References Cited

U.S. PATENT DOCUMENTS

| | | |
|---|---|---|
| 3,773,919 A | 11/1973 | Boswell et al. |
| 3,896,111 A | 7/1975 | Kupchan et al. |
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,270,537 A | 6/1981 | Romaine |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,315,929 A | 2/1982 | Freedman et al. |
| 4,317,821 A | 3/1982 | Miyashita et al. |
| 4,322,348 A | 3/1982 | Asai et al. |
| 4,331,598 A | 5/1982 | Hasegawa et al. |
| RE30,985 E | 6/1982 | Cartaya |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,376,110 A | 3/1983 | David et al. |
| 4,419,446 A | 12/1983 | Howley et al. |
| 4,424,219 A | 1/1984 | Hashimoto et al. |
| 4,450,254 A | 5/1984 | Isley et al. |
| 4,560,655 A | 12/1985 | Baker |
| 4,596,556 A | 6/1986 | Morrow et al. |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,601,978 A | 7/1986 | Karin |
| 4,657,866 A | 4/1987 | Kumar |
| 4,676,980 A | 6/1987 | Segal et al. |
| 4,741,900 A | 5/1988 | Alvarez et al. |
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |

(Continued)

FOREIGN PATENT DOCUMENTS

| | | |
|---|---|---|
| EP | 404097 A2 | 12/1990 |
| EP | 0341735 B1 | 9/1992 |

(Continued)

OTHER PUBLICATIONS

Bennett et al. Chem. Soc. Rev. 2007, 36:1227-1238.*

(Continued)

*Primary Examiner* — Lynn A Bristol
(74) *Attorney, Agent, or Firm* — Duane Morris LLP

(57) ABSTRACT

Modified Fc regions of antibodies and antibody fragments, both human and humanized, and having enhanced stability and efficacy, are provided. Fc regions with core fucose residues removed, and attached to oligosaccharides comprising terminal sialyl residues, are provided. Antibodies comprising homogeneous glycosylation of Fc regions with specific oligosaccharides are provided. Fc regions conjugated with homogeneous glycoforms of monosaccharides and trisaccharides, are provided. Methods of preparing human antibodies with modified Fc using glycan engineering, are provided.

8 Claims, 5 Drawing Sheets
(5 of 5 Drawing Sheet(s) Filed in Color)

(56) References Cited

U.S. PATENT DOCUMENTS

| | | |
|---|---|---|
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A * | 11/1994 | Wong et al. ............ 435/68.1 |
| 5,374,541 A * | 12/1994 | Wong et al. ............ 435/74 |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,716,465 B2 | 5/2014 | Rossi et al. |
| 8,802,438 B2 | 8/2014 | Rossi et al. |
| 8,815,941 B2 | 8/2014 | Withers |
| 8,883,506 B2 | 11/2014 | Rossi et al. |
| 8,906,832 B2 | 12/2014 | Wong et al. |
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |
| 9,434,786 B2 * | 9/2016 | Wang ............ C07K 16/2887 |
| 9,759,726 B2 | 9/2017 | Wong et al. |
| 9,803,177 B2 | 10/2017 | Rossi et al. |
| 9,914,956 B2 | 3/2018 | Wong et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1 | 5/2004 | Wohlstadter |
| 2004/0131692 A1 | 7/2004 | Kreuter et al. |
| 2004/0137557 A1 * | 7/2004 | DeFrees et al. ............ 435/68.1 |
| 2004/0204354 A1 | 10/2004 | Nelson et al. |

(56) References Cited

U.S. PATENT DOCUMENTS

| | | |
|---|---|---|
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0221397 A1 | 10/2005 | Saito |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1 | 3/2007 | Blixt et al. |
| 2007/0065949 A1 | 3/2007 | Hutchens |
| 2007/0207090 A1 | 9/2007 | Giudice |
| 2007/0213278 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng et al. |
| 2009/0317837 A1 | 12/2009 | Wong et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2011/0086408 A1 | 4/2011 | Powers |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0263828 A1 | 10/2011 | Wong et al. |
| 2012/0046346 A1 | 2/2012 | Rossi et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0294859 A1 | 11/2012 | Goletz et al. |
| 2012/0322864 A1 | 12/2012 | Rossi et al. |
| 2012/0322865 A1 | 12/2012 | Rossi et al. |
| 2012/0328646 A1 | 12/2012 | Wong et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0337018 A1 | 12/2013 | Fox |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0302028 A1 | 10/2014 | Zha |
| 2014/0308746 A1 | 10/2014 | Rossi et al. |
| 2015/0087814 A1* | 3/2015 | Wang ............... C07K 16/2887 530/391.9 |
| 2015/0160217 A1 | 6/2015 | Wong et al. |
| 2015/0225766 A1 | 8/2015 | Wong et al. |
| 2015/0309041 A1 | 10/2015 | Wong et al. |
| 2015/0344544 A1* | 12/2015 | Wong .................. C12N 9/24 424/133.1 |
| 2015/0344551 A1 | 12/2015 | Wong et al. |
| 2015/0344559 A1* | 12/2015 | Wong ................ A61K 39/3955 424/133.1 |
| 2015/0344585 A1* | 12/2015 | Wong ................... C07K 16/283 424/133.1 |
| 2015/0344587 A1* | 12/2015 | Wong ................. A61K 31/517 424/133.1 |
| 2016/0009803 A1 | 1/2016 | Rother et al. |
| 2016/0102151 A1* | 4/2016 | Wong ................... C07K 16/18 424/135.1 |
| 2016/0215061 A1 | 7/2016 | Shaeen |
| 2016/0274121 A1 | 9/2016 | Wong et al. |
| 2016/0280794 A1* | 9/2016 | Wong ................... C07K 16/30 |
| 2016/0289340 A1 | 10/2016 | Wong et al. |
| 2017/0275389 A1 | 9/2017 | Wong et al. |
| 2017/0283878 A1 | 10/2017 | Wong et al. |

FOREIGN PATENT DOCUMENTS

| | | |
|---|---|---|
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-222085 | 8/1993 |
| JP | 05-507068 | 10/1993 |
| JP | 05-339283 A | 12/1993 |
| JP | 11-343295 A | 12/1999 |
| JP | 2005-06008 | 5/2000 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 | 5/1993 |
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO-96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO-97/17852 A1 | 5/1997 |
| WO | WO 97/037705 | 10/1997 |
| WO | WO 98/00558 A1 | 1/1998 |
| WO | WO-98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |
| WO | WO 03/040104 A1 | 5/2003 |
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |

(56) References Cited

FOREIGN PATENT DOCUMENTS

| WO | WO 2006/126069 A2 | 11/2006 |
|----|----|----|
| WO | WO 2006/130458 A2 | 12/2006 |
| WO | WO 2007/078873 A1 | 7/2007 |
| WO | WO 2007/133855 * | 11/2007 |
| WO | WO-2007/146847 A2 | 12/2007 |
| WO | WO 2008-020596 A2 | 2/2008 |
| WO | WO 2008/087260 A1 | 7/2008 |
| WO | WO 2008/118013 | 10/2008 |
| WO | WO 2008/133801 A1 | 11/2008 |
| WO | WO 2009/029888 A3 | 3/2009 |
| WO | WO 2010/006315 A2 | 1/2010 |
| WO | WO 2010/009271 A1 | 1/2010 |
| WO | WO 2010/011703 | 1/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/145957 A1 | 11/2011 |
| WO | WO 2012/082635 A1 | 6/2012 |
| WO | WO 2012/094540 A2 | 7/2012 |
| WO | WO 2013/011347 A1 | 1/2013 |
| WO | WO 2013/012066 | 1/2013 |
| WO | WO 2013/024895 A1 | 2/2013 |
| WO | WO 2013/088395 A1 | 6/2013 |
| WO | WO 2013/120066 A1 | 8/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO 2014/031762 A1 | 2/2014 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2016-118090 A1 | 7/2016 |

OTHER PUBLICATIONS

Yamane-Ohnuki et al. mAbs 2009, 1;3:230-236.*
Anthony et al. Science Apr. 18, 2008. 320:373-376.*
Fan et al. JBC vol. 287, No. 14, pp. 11272-11281, Mar. 30, 2012.*
Lin et al. PNAS | Aug. 25, 2015 | vol. 112 | No. 34 | 10611-10616.*
Brennan et al., "Preparation of bispecific antibodies by chemical recombination of monoclonal immunoglobulin G₁ fragments," *Science*, Jul. 5, 1985, 229(4708):81-83.
Brüggemann et al., "Designer mice: the production of human antibody repertoires in transgenic animals," *Year Immunol.*, 1993, 7:33-40.
Capel et al., "Heterogeneity of human IgC Fc receptors," *Immunomethods*, Feb. 1994, 4(1):25-34.
Chothia et al., "Canonical structures for the hypervariable regions of immunoglobulins," *J. Mol. Biol.*, Aug. 20, 1987, 196(4):901-917.
Clackson et al., "Making antibody fragments using phage display libraries," *Nature*, Aug. 15, 1991, 352(6336):624-628.
Clynes et al., "Fc receptors are required in passive and active immunity to melanoma," *Proc. Natl. Acad. Sci. US.A.*, Jan. 20, 1998, 95(2):652-656.
Daëron, "Fc receptor biology," *Annu. Rev. Immunol.*, 1997, 15:203-234.
De Haas et al., "Fcγ receptors of phagocytes," *J. Lab. Clin. Med.*, Oct. 1995, 126(4):330-341.
Gazzano-Santoro et al., "A non-radioactive complement-dependent cytotoxicity assay for anti-CD20 nonclonal antibody," *J. Immunol. Methods*, Mar. 28, 1997, 202(2):163-171.

Guyer et al., "Immunoglobulin binding by mouse intestinal epithelial cell receptors," *J. Immunol.*, Aug. 1976, 117(2):587-593.
Heyman, "Complement and Fc-receptors in regulation of the antibody response," *Immunol. Lett.*, Dec. 1996, 54(2-3):195-199.
Honegger et al., "Yet another numbering scheme for immunoglobulin variable domains: an automatic modeling and analysis tool," *J. Mol. Biol.*, Jun. 8, 2001, 309:657-670.
Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.
Jones et al., "Replacing the complementarity-determining regions in a human antibody with those from a mouse," *Nature*, May 29-Jun. 4, 1986, 321(6069):522-525.
Kaneko et al., "Anti-inflammatory activity of immunoglobulin G resulting from Fc sialylation," *Science*, Aug. 4, 2006, 313(5787):670-673.
Kim et al., "Localization of the site of the murine IgG1 molecule that is involved in binding to the murine intestinal Fc receptor," *Eur. J. Immunol.*, 1994, 24:2429-2434.
Köhler et al., "Continuous cultures of fused cells secreting antibody of predefined specificity," *Nature*, Aug. 7, 1975, 256(5517):495-497.
Lefranc et al., "IMGT, the international ImMunoGeneTics database," *Nucleic Acids Res.*, Jan. 1, 1999, 27(1):209-212.
Marks et al., "By-passing immunization. Human antibodies from V-gene libraries displayed on phage," *J. Mol. Biol.*, Dec. 5, 1991, 222(3):581-597.
Mimura et al., "Role of oligosaccharide residues of IgG1-Fc in FcγRIIb binding," *J. Biol. Chem.*, Dec. 7, 2001, 276(49):45539-45547.
Morimoto et al., "Single-step purification of F(ab')₂ fragments of mouse monoclonal antibodies (immunoglobulins G1) by hydrophobic interaction high performance liquid chromatography using TSKgel Phenyl-5PW," *J. Biochem. Biophys. Methods*, Mar. 1992, 24(1-2):107-117.
Morrison et al., "Chimeric human antibody molecules: mouse antigen-binding domains with human constant region domains," *Proc. Natl. Acad. Sci. U.S.A.*, Nov. 1984, 81(21):6851-6855.
Peipp et al., "Antibody fucosylation differentially impacts cytotoxicity mediated by NK and PMN effector cells," *Blood*, 2008, 112(6):2390-2399.
Presta, "Antibody engineering," *Curr. Opin. Struct. Biol.*, Aug. 1992, 2(4):593-596.
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Riechmann et al., "Reshaping human antibodies for therapy," *Nature*, Mar. 24, 1988, 332(6162):323-327.
Roos et al., "Specific inhibition of the classical complement pathway by C1q-binding peptides," *J. Immunol.*, Dec. 15, 2001, 167(12):7052-7059.
Ruiz et al., "IMGT, the international ImMunoGeneTics database," *Nucl. Acids Res.*, Jan. 1, 2000, 28(1):219-221.
Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcαRIII antibody-dependent cellular toxicity," *J. Biol. Chem.*, Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.

(56) References Cited

OTHER PUBLICATIONS

Tutt et al., "Trispecific F(ab')₃ derivatives that use cooperative signaling via the TCR/CD3 complex and CD2 to activate and redirect resting cytotoxic T cells," *J. Immunol.*, Jul. 1, 1991, 147(1):60-69.
Verhoeyen et al., "Reshaping human antibodies: grafting an antilysozyme activity," *Science*, Mar. 25, 1988, 239(4847):1534-1536.
Woof et al., "Human antibody-Fc receptor interactions illuminated by crystal structures," *Nat. Rev. Immunol.*, Feb. 2004, 4(2):89-99.
Zapata et al., "Engineering linear F(ab')₂ fragments for efficient production in *Escherichia coli* and enhanced antiproliferative activity," *Protein Eng.*, Oct. 1995, 8(10):1057-1062.
U.S. Appl. No. 15/011,543, filed Jan. 30, 2016, Chi-Huey Wong, et al.
U.S. Appl. No. 15/173,496, filed Jun. 3, 2016, Chi-Huey Wong, et al.
U.S. Appl. No. 15/005,930, filed Jan. 25, 2016, Chi-Huey Wong, et al.
U.S. Appl. No. 15/011,544, filed Jan. 30, 2016, Chi-Huey Wong, et al.
Abrahmsén et al, "Analysis of signals for secretion in the staphylococcal protein A gene," *EMBO J.*, Dec. 30, 1985, 4(13B):3901-3906.
Altschul SF et al., "Basic local alignment search tool", *J Mol Biol.* Oct. 5, 1990;215(3):403-10.
Altschul SF, et al., "Gapped BLAST and PSI-BLAST: a new generation of protein database search programs", *Nucleic Acids Res.* Sep. 1, 1997;25(17):3389-402.
Anderson et al., "Stimulation of Natural Killer T Cells by Glycolipids", *Molecules*, May 2013, 18(12), 15662-15688.
Arié et al., "Chaperone function of FkpA, a heat shock prolyl isomerase, in the periplasm of *Escherichia coli*," *Mol. Microbiol.*, Jan. 2001, 39(1):199-210.
Bachmann, *Cellular and Molecular Biology, vol. 2, Chapter 72: Derivations and Genotypes of Some Mutant Derivative of Escherichia coli* K-12, Niedhardt et al., eds., 1987, pp. 1190-1219, American Society for Microbiology, Washingon, D.C.
Baldwin et al., "Monoclonal antibodies in cancer treatment," *Lancet*, Mar. 15, 1986, 327(8481):603-605.
Barbas et al., "Assembly of combinatorial antibody libraries on phage surfaces: the gene III site," *Proc. Natl. Acad. Sci. U.S.A.*, Sep. 15, 1991, 88(18):7978-7982.
Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 91(9):3809-3813.
Barbas et al., "Semisynthetic combinatorial antibody libraries: a chemical solution to the diversity problem," *Proc. Natl. Acad. Sci. U.S.A.*, May 15, 1992, 89(10):4457-4461.
Barnes et al., "Methods for growth of cultured cells in serum-five medium," *Anal. Biochem.*, Mar. 1, 1980, 102(2):255-270.
Baselga J, et al., "Phase II study of weekly intravenous recombinant humanized anti-p185HER2 monoclonal antibody in patients with HER2/neu-overexpressing metastatic breast cancer",*J Clin Oncol.* Mar. 1996;14(3):737-44.
Bass et al., "Hormone phage: an enrichment method for variant proteins with altered binding properties," *Proteins*, 1990, 8(4):309-314.
Beck A., "Biosimilar, biobetter and next generation therapeutic antibodies" *MAbs.* Mar.-Apr. 2011;3(2):107-10. Epub Mar. 1, 2011.
Berra et al., "Correlation between ganglioside distribution and histological grading of human astrocytomas," *Int. J. Cancer*, Sep. 15, 1985, 36(3):363-366.
Birklé et al., "Role of tumor-associated gangliosides in cancer progression," *Biochimie*, Mar.-Apr. 2003, 85(3-4):455-463.
Bobo et al., "Convection-enhanced delivery of macromolecules in the brain," *Proc. Natl. Acad. Sci. U.S.A.*, Mar. 15, 1994, 91(6) 2076-2080.

Boerner et al., "Production of antigen-specific human monoclonal antibodies from in vitro-primed human splenocytes," *J. Immunol.*, Jul. 1, 1991, 147(1):86-95.
Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.
Brimble et al., "The cell surface glycosphingolipids SSEA-3 and SSEA-4 are not essential for human ESC pluripotency," *Stem Cells*, Jan. 2007, 25(1):54-62.
Brodeur et al., *Monoclonal Antibody Production Techniques and Applications, Chapter 4: Mouse-Human Myeloma Partners for the Production of Heterohybridomas*, Schook, ed., 1987, pp. 51-63, Marcel Dekker, Inc., New York.
Carter et al., "High level *Escherichia coli* expression and production of a bivalent humanized antibody fragment," *Nature Biotechnology*, Feb. 1992, 10(2):163-167.
Carter et al., "Humanization of an anti-p185$^{HER2}$ antibody for human cancer therapy," *Proc. Natl. Acad. Sci. U.S.A.*, May 15, 1992, 89(10):4285-4289.
Carter PJ. "Potent antibody therapeutics by design" *Nat Rev Immunol.* May 2006;6(5):343-357.
Chang et al., "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.
Chen et al., "Chaperone activity of DsbC," *J. Bio. Chem.*, Jul. 9, 1999, 274(28):19601-19605.
Chen et al., "Selection and analysis of an optimized anti-VEGF antibody: crystal structure of an affinity-matured Fab in complex with antigen," *J. Mol. Biol.*, Nov. 5, 1999, 293(4):865-881.
Chen et al., "Selective killing of transformed cells by cyclin/cyclin-dependent kinase 2 antagonists," *Proc. Natl. Acad. Sci. U.S.A.*, Apr. 13, 1999, 96(8):4325-4329.
Clark EA et al., "Structure, function, and genetics of human B cell-associated surface molecules" *Adv Cancer Res.* 1989;52:81-149.
Cunningham et al., "High-resolution epitope mapping of hGH-receptor interactions by alanine-scanning mutagenesis," *Science*, Jun. 2, 1989, 244(4908):1081-1085.
de Almeida et al., "Thiacycloalkynes for copper-free click chemistry," *Angew. Chem. Int. Ed. Engl.*, Mar. 5, 2012, 51(10):2443-2447.
Durrant et al., "Immunology in the clinic review series; focus on cancer: glycolipids as targets for tumour immunotherapy," *Clin. Exp. Immunol.*, Feb. 2012, 167(2):206-215.
Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.
Engels et al., "Gene synthesis [new synthetic methods (77)]," *Angew. Chem. Int. Ed. Engl.*, Jun. 1989, 28(6):716-734.
Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.
Fishwild et al., "High-avidity human IgGK monoclonal antibodies from a novel strain of minilocus transgenic mice," *Nature Biotechnol.*, Jul. 1996, 14(7):845-851.
Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential ganglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.
Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.
Fujita M et al., "A novel disaccharide substrate having 1,2-oxazoline moiety for detection of transglycosylating activity of endoglycosidases" *Biochim Biophys Acta.* Sep. 3, 2001;1528(1):9-14.

(56) References Cited

OTHER PUBLICATIONS

Galfrè et al., "Preparation of monoclonal antibodies: strategies and procedures," *Methods Enzymol.*, 1981, 73(Pt B):3-46.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.
GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [Streptomyces plicatus]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
Gerson et al., "ESR. Spectra and Structures of Radical Anions in the Dibenzo [a, e]cyclooxtene Series," *Helvetica Chinica Acta*, Jan. 1, 1976, 59(6): 2038-2048.
Gill et al., "Direct brain infusion of glial cell line-derived neurotrophic factor in Parkinson disease," *Nature Med.*, May 2003, 9(5):589-595 and Addendum from Apr. 2006, 12(4):479.
Goding, *Monoclonal Antibodies: Principles and Practice 2nd ed., Chapter 3: Production of Monoclonal Antibodies*, 1986, pp. 59-103, Academic Press, London.
Golkowski et al., "Strategy for catch and release of azide-tagged biomolecules utilizing a photolabile strained alkyne construct," *Organic and Biomolecular Chemistry*, Jan. 1, 2012, 10(23):4496.
Goochee CF et al., "The oligosaccharides of glycoproteins: bioprocess factors affecting oligosaccharide structure and their effect on glycoprotein properties", *Biotechnology* (N Y). Dec. 1991;9(12):1347-55.
Gordon et al., "Reactivity of biarylazacyclooctynones in copper-free click chemistry," *J. Am. Chem. Soc.*, Jun. 6, 2012, 134(22): 9199-9208.
Gottschling et al., "Stage-specific embryonic antigen-4 is expressed in basaloid lung cancer and associated with poor prognosis," *Eur. Respir. J*, Mar. 2013, 41(3):656-663.
Graham et al., "Characteristics of a human cell line transformed by DNA from human adenovirus type 5," *J. Gen. Virol.*, Jul. 1977, 36(1):59-72.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Green, "Targeting targeted therapy," *N. Engl. J. Med.*, May 20, 2004, 350(21):2191-2193.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli*," *J. Immunol.*, Jun. 1, 1994, 152(11):5368-5374.
Guss et al., "Structure of the IgG-binding regions of streptococcal protein G," *EMBO J.*, Jul. 1986, 5(7):1567-1575.
Hakomori et al., "Glycosphingolipid antigens and cancer therapy," *Chem. Biol.*, Feb. 1997, 4(2):97-104.
Hakomori, "Glycosylation defining cancer malignancy: new wine in an old bottle," *Proc. Natl. Acad. Sci. U.S.A.*, Aug. 6, 2002, 99(16):10231-10233.
Hara et al., "Overproduction of penicillin-binding protein 7 suppresses thermosensitive growth defect at low osmolarity due to an spr mutation of *Escherichia coli*," *Microbial Drug Resistance*, Spring 1996, 2(1):63-72.
Harris, "Production of humanized monoclonal antibodies for in vivo imaging and therapy," *Biochem. Soc. Transactions*, Nov. 1995, 23(4):1035-1038.
Hawkins et al., "Selection of phage antibodies by binding affinity. Mimicking affinity maturation," *J. Mol. Biol.*, 1992, 226(3):889-896.

Hinman et al., "Preparation and characterization of monoclonal antibody conjugates of the calicheamicins: a novel and potent family of antitumor antibiotics," *Cancer Res.*, Jul. 15, 1993, 53(14):3336-3342.
Hogrefe et al., "A bacteriophage lambda vector for the cloning and expression of immunoglobulin Fab fragments on the surface of filamentous phage," *Gene*, Jun. 15, 1993, 128(1):119-126.
Holliger et al., "'Diabodies': small bivalent and bispecific antibody fragments," *Proc. Natl. Acad. Sci. U.S.A.*, Jul. 15, 1993, 90(14):6444-6448.
Hoogenboom et al., "By-passing immunisation. Human antibodies from synthetic repertoires of germline $V_H$ gene segments rearranged in vitro," *J. Mol. Biol.*, Sep. 20, 1992, 227(2):381-388.
Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.
Huang et al., "Carbohydrate-based vaccines with a glycolipid adjuvant for breast cancer," *Proc. Natl. Acad. Sci. U.S.A.*, Feb. 12, 2013, 110(7):2517-2522.
Hung et al., "Investigation of SSEA-4 binding protein in breast cancer cells," *J. Am. Chem. Soc.*, Apr. 24, 2013, 135(16):5934-5937.
Hurle et al., "Protein engineering techniques for antibody humanization," *Curr. Opin. Biotechnol.*, Aug. 1994, 5(4):428-433.
Inouye et al., "Single-step purification of $F(ab')_{2\mu}$, fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.
Jackson et al., "In vitro antibody maturation: Improvement of a high affinity, neutralizing antibody against IL-1β," *J. Immunol.*, Apr. 1, 1995, 154(7):3310-3319.
Jenkins N, Curling EM., "Glycosylation of recombinant proteins: problems and prospects", *Enzyme Microb Technol.* May 1994;16(5):354-64.
Jewett et al., "Synthesis of a fluorogenic cyclooctyne activate by Cu-free click chemistry," *Org. Lett.*, Nov. 18, 2011, 13(22):5937-5939.
Jones et al., "Rapid PCR-cloning of full-length mouse immunoglobulin variable regions," *Nature Biotechnol.*, Jan. 1991, 9(1):88-89.
Jones, "Analysis of polypeptides and proteins," *Adv. Drug Delivery Rev.*, Jan.-Apr. 1993, 10(1):29-90.
Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells,"*EMBO J.*, 1983, 2(12):2355-2361.
Karlin S. et al., "Methods for assessing the statistical significance of molecular sequence features by using general scoring schemes", *Proc Natl Acad Sci U S A.* Mar. 1990;87(6):2264-8.
Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.
Kontermann, "Intrabodies as therapeutic agents," *Methods*, Oct. 2004, 34(2):163-170.
Kostelny et al., "Formation of a bispecific antibody by the use of leucine zippers," *J. Immunol.*, Mar. 1, 1992, 148(5):1547-1553.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell.* Apr. 8, 1988;53(1):45-53.
Kudo et al., "Up-regulation of a set of glycosyltransferase genes in human colorectal cancer," *Lab. Invest.*, Jul. 1998, 78(7):797-811.

(56) References Cited

OTHER PUBLICATIONS

Lau et al., "N-Glycans in cancer progression," *Glycobiology*, Oct. 2008, 18(10):750-760.

Lee et al., "Bivalent antibody phage display mimics natural immunoglobulin," *J. Immunol. Methods*, Jan. 2004, 284(1-2):119-132.

Lee et al., "High-affinity human antibodies from phage-displayed synthetic Fab libraries with a single framework scaffold," *J. Mol. Biol.*, Jul. 23, 2004, 340(5):1073-1093.

Lehninger, *Biochemistry: The Molecular Basis of Cell Structure and Function*, 2nd ed., 1975, pp. 73-75, Worth Publishers, New York.

Leung et al., "A method for random mutagenesis of a defined DNA segment using a modified polymerase chain reaction," *Technique—A Journal of Methods in Cell and Molecular Biology*, Aug. 1989, 1(1):11-15.

Lindmark et al., "Binding of immunoglobulins to protein A and immunoglobulin levels in mammalian sera," *J. Immunol. Meth.*, Aug. 12, 1983, 62(1):1-13.

Liu C, et al., "Expansion of spleen myeloid suppressor cells represses NK cell cytotoxicity in tumor-bearing host" *Blood*. May 15, 2007;109(10):4336-42. Epub Jan. 23, 2007.

Liu et al., "Eradication of large colon tumor xenografts by targeted delivery of maytansinoids," *Proc. Natl., Acad. Sci. U.S.A.*, Aug. 6, 1996, 93(16):8618-8623.

LoBuglio et al., "Mouse/human chimeric monoclonal antibody in man: kinetics and immune response," *Proc. Natl. Acad. Sci. U.S.A.*, Jun. 1989, 86(11):4220-4224.

Lode et al., "Targeted therapy with a novel enediyene antibiotic calicheamicin $\Theta^I_1$ effectively suppresses growth and dissemination of liver metastases in a syngeneic model of murine neuroblastoma," *Cancer Res.*, Jul. 15, 1998, 58(14):2925-2928.

Longberg et al., "Antigen-specific human antibodies from mice comprising four distinct genetic modifications," *Nature*, Apr. 28, 1994, 368(6474):856-859.

Lonberg et al., "Human antibodies from transgenic mice," *Int. Rev. Immunol.*, 1995, 13(1):65-93.

Louis et al., "The 2007 WHO classification of tumours of the central nervous system," *Acta. Neuropathol.*, Aug. 2007, 114(2):97-109.

Lu et al., "Single chain anti-c-Met antibody conjugated nanoparticles for in vivo tumor-targeted imaging and drug delivery," *Biomaterials*, Apr. 2011, 32(12):3265-3274.

Macfarlane GT, et al., "Formation of glycoprotein degrading enzymes by Bacteroides fragilis" *FEMS Microbiol Lett*. Jan. 15, 1991;61(2-3):289-93.

Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.

Mandler et al., "Modifications in synthesis strategy improve the yield and efficacy of geldanamycin-herceptin immunoconjugates," *Bioconjugate Chem.*, Jul.-Aug. 2002, 13(4)786-791.

Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.

Månsson et al., "Characterization of new gangliosides of the lactotetraose series in murine xenografts of a human glioma cell line," *FEBS Lett.*, May 26, 1986, 201(1):109-113.

Marasco et al., "Design, intracellular expression, and activity of a human anti-human immunodeficiency virus type 1 gp120 single-chain antibody," *Proc. Natl. Acad. Sci. U.S.A.*, Aug. 15, 1993, 90(16):7889-7893.

Marasco, "Intrabodies: turning the humoral immune system outside in for intracellular immunization," *Gene Therapy*, Jan. 1997, 4(1):11-15.

Marks et al., "By-passing immunization: Building high affinity human antibodies by chain shuffling," *Nature Biotechnology*, Jul. 1992, 10(7):779-783.

Mather et al., "Culture of testicular cells in hormone-supplemented serum-five medium," *Annals N.Y. Acad. Sci.*, 1982, 383:44-68.

Mather, "Establishment and characterization of two distinct mouse testicular epithelial cell lines," *Biol. Reprod.*, Aug. 1980, 23(1):243-252.

Matsuda et al., "Structure and physical map of 64 variable segments in the 3' 0.8-megabase region of the human immunoglobulin heavy-chain locus," *Nature Genet.*, Jan. 1993, 3(1):88-94.

McCafferty et al., "Phage antibodies: Filamentous phage displaying antibody variable domains," *Nature*, Dec. 6, 1990, 348:552-554.

Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.

Meyer, "Malignant gliomas in adults," *N. Engl. J. Med.*, Oct. 23, 2008, 359(17):1850.

Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.

Morelle, W. et al., "The Mass Spectrometric Analysis of Glycoproteins and their Glycan Sturctures", *Review in Current Analytical Chemistry*, vol. 1, No. 1 (2005), pp. 29-57.

Mori K, et al., "Non-fucosylated therapeutic antibodies: the next generation of therapeutic antibodies" *Cytotechnology*. Dec. 2007;55(2-3):109-14. Epub Oct. 31, 2007.

Morrison, "Immunology. Success in specification," *Nature*, Apr. 28, 1994, 368(6474):812-813.

Munson et al., "Ligand: a versatile computerized approach for characterization of ligand-binding systems," *Anal. Biochem.*, Sep. 1, 1980, 107(1):220-239.

Neuberger et al., "Recombinant antibodies possessing novel effector functions," *Nature*, Dec. 13-19, 1984, 312(5995):604-608.

Neuberger, "Generating high-avidity human Mabs in mice," *Nature Biotechnol.*, Jul. 1996, 14(7):826.

Nicolaou et al., "Calicheamicin $\Theta^I_1$: A rationally designed molecule with extremely potent and selective DNA cleaving properties and apoptosis inducing activity," *Angew. Chem. Intl. Ed. Engl.*, Feb. 1, 1994, 33(2):183-186.

Niculescu-Duvaz et al., "Antibody-directed enzyme prodrug therapy (ADEPT): A review," *Adv. Drg. Del. Rev.*, Jul. 7, 1997, 26(2-3):151-172.

Noto et al., "CD44 and SSEA-4 positive cells in an oral cancer cell line HSC-4 possess cancer stem-like cell characteristics," *Oral Oncol.*, Aug. 2013, 49(8):787-795.

Orlandi et al., "Cloning immunoglobulin variable domains for expression by the polymerase chain reaction," *Proc. Natl. Acad. Sci. U.S.A.*, May 1989, 86(10):3833-3837.

Ørum et al., "Efficient method for constructing comprehensive murine Fab antibody libraries displayed on phage." *Nucleic Acids Res.*, Sep. 25, 1993, 21(19):4491-4498.

Papanastassiou et al., "The potential for efficacy of the modified (ICP 34.5⁻) herpes simplex virus HSV1716 following intratumoural injection into human malignant glioma: a proof of principle study," *Gene Therapy*, Mar. 2002, 9(6):398-406.

Pearlman et al., *Peptide and Protein Drug Delivery, Chapter 6: Analysis of Protein Drugs*, Lee, ed., 1991, pp. 247-301, Marcel Dekker Publishing, New York.

Plückthun, "Mono- and bivalent antibody fragments produced in *Escherichia coli*: Engineering, folding and antigen binding," *Immunol. Rev.*, Dec. 1992, 130:151-188.

Plückthun, *Handbook of Experimental Pharmacology, vol. 113: The Pharacology of Monoclonal Antibodies, Chapter 11: Antibodies from Escherichia coli*, Rosenberg et al., eds., 1994, pp. 269-315, Springer-Verlag, Berlin.

Poloukhtine et al., "Selective labeling of living cells by a photo-triggered click reaction, " *J. Am. Chem. Soc.*, Nov. 4, 2009, 131(43):15769-15776.

Presta et al., "Humanization of an antibody directed against IgE," *J. Immunol.*, Sep. 1, 1993, 151(5):2623-2632.

Presta et al., "Humanization of an anti-vascular endothelial growth factor monoclonal antibody for the therapy of solid tumors and other disorders," *Cancer Res.*, Oct. 15, 1997, 57(20):4593-4599.

(56) References Cited

OTHER PUBLICATIONS

Presta, "Antibody engineering," *Curr. Opin. Biotechnol.*, Aug. 1992, 3(4):394-398.
Proba et al., "Functional antibody single-chain fragments from the cytoplasm of *Escherichia coli*: influence of thioredoxin reductase (TrxB)," *Gene*, Jul. 4, 1995, 159(2):203-207.
Puigbò P, Guzmán E, Romeu A, Garcia-Vallvé S. Optimizer: a web server for optimizing the codon usage of DNA sequences. *Nucleic Acids Res*. Jul. 2007;35(Web Server issue):W123-31. Epub Apr. 16, 2007.
Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.
Reyes et al., "Expression of human β-interferon cDNA under the control of a thymidine kinase promoter from herpes simplex virus," *Nature*, Jun. 17, 1982, 297(5867):598-601.
Roguska et al., "Humanization of murine monoclonal antibodies through variable domain resurfacing," *Proc. Natl. Acad. Sci. U.S.A.*, Feb. 1, 1994, 91(3):969-973.
Rowland et al, "Drug localisation and growth inhibition studies of vindesine-monoclonal anti-CEA conjugates in a human tumour xenograft," *Cancer Immunol. Immunother.*, 1986, 21(3):183-187.
Saito et al., "Expression of globo-series gangliosides in human renal cell carcinoma," *Jpn. J. Cancer Res.*, Jul. 1997, 88(7):652-659.
Saito et al., "Human α2,3-sialyltransferase (ST3Gal II) is a stage-specific embryonic antigen-4 synthase," *J. Biol. Chem.*, Jul. 18, 2003, 278(29):26474-26479.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Schenkel-Brunner, *Human Blood Groups, Chapter 8: P System*, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Sell, "Cancer-associated carbohydrates identified by monoclonal antibodies," *Hum. Pathol.*, Oct. 1990, 21(10):1003-1019.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Sidhu et al., "Phage-displayed antibody libraries of synthetic heavy chain complementarity determining regions," *J. Mol. Biol.*, Apr. 23, 2004, 338(2):299-310.
Siebenlist et al., "*E. coli* RNA polymerase interacts homologously with two different promoters," *Cell*, Jun. 1980, 20(2):269-281.
Simmons et al., "Expression of full-length immunoglobulins in *Escherichia coli*: Rapid and efficient production of aglycosylated antibodies," *J. Immunol. Methods*, May 1, 2002, 263(1-2):133-147.
Sims et al., "A humanized CD18 antibody can block function without cell destruction," *J. Immunol.*, Aug. 15, 1993, 151(4):2296-2308.
Skerra, "Bacterial expression of immunoglobulin fragments," *Curr. Opinion in Immunol.*, Apr. 1993, 5(2):256-262.
Slamon DJ, et al., "Human breast cancer: correlation of relapse and survival with amplification of the HER-2/neu oncogene" *Science*, Jan. 9, 1987; 235(4785):177-82.
Sletten et al., "Bioorthogonal Chemistry: Fishing for Selectivity in a Sea of Functionality," *Angew. Che. Int. Ed. Engl.*, Aug. 27, 2009, 48(38):6974-6998.
Smith RA et al., "The active form of tumor necrosis factor is a trimer" *J Biol Chem*. May 25, 1987;262(15):6951-4.
Smyth MJ, et al., "CD4+CD25+ T regulatory cells suppress NK cell-mediated immunotherapy of cancer" *J Immunol*. Feb. 1, 2006;176(3):1582-7.
Suresh et al., "Bispecific monoclonal antibodies from hybrid hybridomas," *Methods in Enzymology*, 1986, 121:210-228.

Suzuki E, et al., "A nonfucosylated anti-HER2 antibody augments antibody-dependent cellular cytotoxicity in breast cancer patients" *Clin Cancer Res*. Mar. 15, 2007;13(6):1875-82.
Svennerholm et al., "Human brain gangliosides: Developmental changes from early fetal stage to advanced age," *Biochim. Biophys. Acta*, Sep. 25, 1989, 1005(2):109-117.
Syrigos et al., "Antibody directed enzyme prodrug therapy (ADEPT): a review of the experimental and clinical considerations," *Anticancer Research*, Jan.-Feb. 1999, 19(1A):605-614.
Takeda et al., "Construction of chimaeric processed immunoglobulin genes containing mouse variable and human constant region sequences," *Nature*, Apr. 4-10, 1985, 314(6010):452-454.
Taylor-Papadimitriou et al., "Exploiting altered glycosylation patterns in cancer: Progress and challenges in diagnosis and therapy," *Trends Biotechnol.*, Jun. 1994, 12(6):227-233.
Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.
Tomlinson et al., "The repertoire of human germline $V_H$ sequences reveals about fifty groups of $V_H$ segments with different hypervariable loops," *J. Mol. Biol.*, Oct. 5, 1992, 227(3):776-798.
Traunecker et al., "Bispecific single chain molecules (Janusins) target cytotoxic lymphocytes on HIV infected cells," *EMBO J.*, Dec. 1991, 10(12):3655-3659.
Traylor et al., "Gangliosides of human cerebral astrocytomas," *J. Neurochem.*, Jan. 1980, 34(1):126-131.
Tsai TI, et al., "Effective sugar nucleotide regeneration for the large-scale enzymatic synthesis of Globo H and SSEA4" *J Am Chem Soc*. Oct. 2, 2013;135(39):14831-9, Epub Sep. 17, 2013.
Tyagarajan K et al., "Exoglycosidase purity and linkage specificity: assessment using oligosaccharide substrates and high-pH anion-exchange chromatography with pulsed amperometric detection" *Glycobiology*. Jan. 1996;6(1):83-93.
Urlaub et al., "Isolation of Chinese hamster cell mutants deficient in dihydrofolate reductase activity." *Proc. Natl. Acad. Sci. U.S.A.*, Jul. 1980, 77(7):4216-4220.
Valentine MA, et al., "Phosphorylation of the CD20 phosphoprotein in resting B lymphocytes. Regulation by protein kinase C" *J Biol Chem*. Jul. 5, 1989;264(19):11282-7.
van Beek et al., "Increased sialic acid density in surface glycoprotein of transformed and malignant cells—a general phenomenon?" *Cancer Res.*, Nov. 1973, 33(11):2913-2922.
Van Meir et al., "Exciting new advances in neuro-oncology: the avenue to a cure for malignant glioma," *CA Cancer J. Clin.*, May-Jun. 2010, 60(3):166-193.
Van Slambrouck et al., "Clustering of monosialyl-Gb5 initiates downstream signalling events leading to invasion of MCF-7 breast cancer cells," *Biochem. J.*, Feb. 1, 2007, 401(3):689-699.
Vaswani et al., "Humanized antibodies as potential therapeutic drugs," *Ann. Allergy, Asthma Immunol.*, Aug. 1998, 81(2):105-116, 119.
Vermeer AW et al., "The thermal stability of immunoglobulin: unfolding and aggregation of a multi-domain protein" *Biophys J*. Jan. 2000;78(1):394-404.
Wang et al., "Glycan microarray of Globo H and related structures for quantitative analysis of breast cancer," *Proc. Natl. Acad. Sci. U.S.A.*, Aug. 19, 2008, 105(33):11661-11666.
Ward et al., "Binding activities of a repertoire of single immunoglobulin variable domains secreted from *Escherichia coli*," *Nature*, Oct. 12, 1989, 341(6242):544-546.
Waterhouse et al., "Combinatorial infection and in vivo recombination: a strategy for making large phage antibody repertoires," *Nuc. Acids Res.*, May 11, 1993, 21(9):2265-2266.
Wikstrand et al., "Monoclonal antibody therapy of human gliomas: Current status and future approaches," *Cancer Metastasis Rev.*, 1999, 18(4):451-464.
Williams et al., "Cloning and sequencing of human immunoglobulin V lambda gene segments." *Eur. J. Immunol.*, Jul. 1993, 23(7):1456-1461.
Winter et al., "Making antibodies by phage display technology," *Annu. Rev. Immunol.*, 1994, 12:433-455.

(56) References Cited

OTHER PUBLICATIONS

Yansura et al., "Nucleotide sequence selection for increased expression of heterologous genes in *Escherichia coli*," Methods: A Companion to Methods in Enzymol., Aug. 1992, 4(2):151-158.
Ye et al., "Stage-specific embryonic antigen 4 expression in epithelial ovarian carcinoma," *Int. J. Gynecol. Cancer*, Aug. 2010, 20(6):958-964.
Yelton et al., "Affinity maturation of the BR96 anti-carcinoma antibody by codon-based mutagenesis." *J. Immunol.*, Aug. 15, 1995, 155(4):1994-2004.
Yu et al., "Anti-GD2 antibody with GM-CSF, interleukin-2, and isotretinoin for neuroblastoma," *N. Engl. J. Med.*, Sep. 30, 2010, 363(14):1324-1334.
Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.
Zhang et al., "Selection of tumor antigens as targets for immune attack using immunohistochemistry: I. Focus on gangliosides," *Int. J. Cancer*, Sep. 26, 1997, 73(1):42-49.
International Search Report and Written Opinion issued for International application No. PCT/US2015/032738, dated Oct. 20, 2015, 15 pages.
International Search Report and Written Opinion issued for International application No. PCT/US2015/032744, dated Oct. 2, 2015, 12 pages.
International Search Report and Written Opinion issued for International application No. PCT/US2015/032740, dated Oct. 26, 2015, 13 pages.
International Search Report and Written Opinion issued for International application No. PCT/US2015/032737, dated Oct. 1, 2015, 13 pages.
International Search Report and Written Opinion issued for International application No. PCT/US2015/032745, dated Oct. 8, 2015, 13 pages.
International Search Report issued for International application No. PCT/US2015/049014, dated Dec. 14, 2015, 3 pages.
International Search Report issued for International application No. PCT/US15/22977, dated Jun. 22, 2015, 3 pages.
International Search Report issued for International application No. PCT/US15/40199, dated Mar. 2, 2016, 6 pages.
European Search Report issued in connection with corresponding European Patent Application No. 15181446.4, dated Dec. 7, 2015, 10 pages.
Extended European Search Report dated Jan. 5, 2016 in European Patent Application No. 13830785.5, in 10 pages.
Abbas et al, "Functional diversity of helper T lymphocytes," *Nature*, Oct. 31, 1996, 383(6603):787-793.
Achtman, M., Epidemic Spread and Antigenic Variability of Neisseria Meningitidis, Trends Microbial 1995, 3, 186-192.
Adam et al., "Proteomic profiling of mechanistically distinct enzyme classes using a common chemotype," *Nat. Biotechnol.*, Aug. 2002, 20(8):805-809.
Agard, N. et al., A Strain-Promoted [3+2]Azide-Alkyne Cycloaddition for Covalent Modification of Biomolecules in Living Systems, J. Am. Chem. Soc. 2004, 126, 15046-15047.
Ahmadi, T. S. et al., Shape-Controlled Synthesis of Colloidal Platinum Nanoparticles, Science, 272, 1924 (1996).
Ahmed et al.,Structural Characterization of Anti-Inflammatory Immunoglobulin G Fc Proteins, K Mol Biol (2014) 426, 3166-3179.
Altevogt, Peter et al., Different Patterns of Lectin Binding and Cell Surface Sialylation Detected on Related High- and Low-Metastatic Tumor Lines, Cancer Res. 43, 5138-5144, 1983.
Amin, M. N. et al. Synthetic glycopeptides reveal the glycan specificity of HIV-neutralizing antibodies. Nat. Chem Biol. 9, 521-526, (2013.
Andrews et al., Synthesis and influenza virus sialidase inhibitory activity of analogues of 4-Guanidino-Neu5Ac2en (Zanamivir modified in the glycerol side-chain. Eur J Med Chem Jul.-Aug. 1999;34(7-8):563-74.

Angata et al., "Chemical diversity in the sialic acids and related α-keto acids: an evolutionary perspective," *Chem. Rev.*, Feb. 2002, 102(2):439-469.
Arase et al., "NK1.1$^+$ CD4$^+$ CD8$^-$ thymocytes with specific lymphokine secretion," *Eur. J. Immunol.*, Jan. 1993, 23(1):307-310.
Aspeslagh et al., "Galactose-modified iNKT cell agonists stabilized by an induced fit of CD1d prevent tumour metastasis," *EMBO J.*, Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Banchereau et al., "Dendritic cells and the control of immunity," *Nature*, Mar. 19, 1998, 392(6673):245-252.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barouch, D. H. Challenges in the development of an HIV-I vaccine. Nature 455, 613-619, (2008).
Barry, C.S. et al., 'Naked' and Hydrated Confirmers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baskin, J.M.; Amacher, S. L.; Bertozzi, C.R."In vivo imaging of membraneassociated glycans in developing zebrafish." Science 2008, 320, 664-667.
Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Baz et al., Emergence of oseltamivir-resistant pandemic H1N1 virus during prophylaxis. N. Engl J Med. Dec. 3, 2009;361(23):2296-7. doi: 10.1056/NEJMc0910060. Epub Nov. 11, 2009.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated By The Use of Momoclonal Antibodies: The Example of the Anti-Proinsulin Antibody, J. Histochem. Cytochem, 43: 881-886, (1995).
Berge, Steven et al. J. Pharmaceutical Sciences (1977) 66: 1-19.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," *Glycobiology*, Feb. 2010, 20(2):148-157.
Blixt, O. et al. Printed covalent glycan array for ligand profiling of diverse glycan binding proteins. Proc. Natl. Acad. Sci. U.S. A. 101, 17033-17038, (2004.
Boens, N. et al., "Fluorescent indicators based on BODIPY." Chem. Soc. Rev. 2012, 41, 1130-1172.
Borg et al., "CD1d-lipid-antigen recognition by the semi-invariant NKT T-cell receptor," *Nature*, Jul. 5, 2007, 448(7149):44-49.
Bosmann et al., "Enzyme activity in invasive tumors of human breast and colon," *Proc. Natl. Acad. Sci. USA*, May 1974, 71(5):1833-1837.

(56) References Cited

OTHER PUBLICATIONS

Bost, Kenneth et al., Antibodies Against A Peptide Sequence Within The HIV Envelope Protein Crossreacts With Human Interleukin-2, Immunol. Invest., 17: 577-586 (1988).
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell in Situ Using 16S rRNA-Targeted Probes, Biotechniques, 13, 928-931 (1992).
Bricard et al., "Enrichment of human $CD4^{30}$ $V\alpha 24/V\beta 11$ invariant NKT cells in intrahepatic malignant tumors," *J. Immunol.*, Apr. 15, 2009, 182(2):5140-5151.
Bruchez, Marcel et al. Semiconductor Nanocrystals as Fluorescent Biological Labels, Science 281:2013-2016, 1998.
Buchini et al., "Towards a new generation of specific *Trypanosoma cruzi* trans-sialidase inhibitors," *Angew. Chem. Int. Ed. Engl.*, 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.
Carlsson, Jan et al., Protein Thiolation and Reversible Protein-Protein Conjugation, Biochem J 173: 723-737 (1978).
Carter, A rationale for using steroids in the treatment of severe cases of H5N1 avian influenza. J Med Microbiol. Jul. 2007;56(Pt 7):875-83.
Centers for Disease Control and Prevention (CDC), "Influenza activity—United States and worldwide, 2007-08 season" *MMWR*, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasensitive Nonisotopic Detection, Science 281:2016-2018 (1998).
Chandler et al., Synthesis of the potent influenza neuraminidase inhibitor 5-guanidino Neu5Ac2en. X-Ray molecular structure of 5-acetaminido-4amino-2,6-anahydro-3,4,5-tryoxy-D-erythoro-L-gluco-nononic acid. J Chem Soc Perkin Trans 1. 1995; 1173-1180.
Chang, S. H. et al. Glycan array on aluminum oxide-coated glass slides through phosphonate chemistry. J. Am. Chem. Soc. 132, 13371-13380, (2010).
Chang et al., "Potent immune-modulating and anticancer effects of NKT cell stimulatory glycolipids," *Proc. Nad. Acad. Sci. USA*, Jun. 19, 2007, 104(25):10299-10304.
Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.
Chari, Ravi et al., Immunoconjuates Containing Novel Maytansinoids: Promising Anticancer Drugs Cancer Research 52: 127-131 (1992).
Chauhan, D. P.; Saha, T.; Lahiri, M.; Talukdar, P. "BODIPY based 'click on' fluorogenic dyes: application in live cell imaging." Tetrahedron Lett. 2014, 55, 244-247.
Cheng, Peter et al., Oseltamivir-and Amandtadine-resistant Influenza Viruses A (H1N1), Emerg. Infect. Dis., Jun. 2009, 15(6): 966-968.
Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.
Chiang et al., Ethyl caffeate suppresses NF-kappaB activation and its downstream inflammatory mediators, iNOS, COX-2, and PGE2 in vitro or in mouse skin. Br J Pharmacol. Oct. 2005; 146(3):352-63.
Chiari, M. et al., Advanced Polymers for Molecular Recognition and Sensing at the Interface. J Chromatography B, Apr. 15, 2008, 866(1-2):89-103.

Childs et al., Receptor-Binding Specificity of Pandemic Influenza A (H1N1) 2009 Virus Determined by Carbohydrate Microarray. Nat. Biotechnol. 2009, 27(9): 797-799.
Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.
Chong et al., Influenza Virus Sialidase: Effect of Calcium on Steady-State Kinetic Parameters, Biochim. Biophys. Acta, Mar. 8, 1991, 1077(1): 65-71.
Chothia et al., "Domain association in immunoglobulin molecules. The packing of variable domains," *J. Mol Biol.*, Dec. 5, 1985, 186(3):651-663.
Codelli, J. A. et al., Second-Generation Difluorinated Cyclooctynes for Copper-Free Click Chemistry, J. Am. Chem. Soc. 2008, 130, 11486-11493.
Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.
Coligan et al., Current Protocols in Immunology, sections 2.5.1-2. 6.7, 1991.
Collins et al., Crystal Structures of Oseltamivir-Resistant Influenza Virus Neuraminidase Mutants, Nature, Jun. 26, 2008, 453(7199):1258-1261.
Connor, Robert et al., Receptor Specifcity in Human, Avian, and Equine H2 and H3 Influenza Virus Isolates, Virology, 205: 17, 1994.
Cox et al., New Options for the Prevention of Influenza, N. Engl. J. Med. Oct. 28, 1999, 341(18): 1387-1388.
Cragg, M.S. et al., Complement-Mediated Lysis by Ant-CD20 mAb Correlates with Segregation into Lipid Rafts, Blood 101 (2003) 1045-1052.
Cragg, M.S. et al., Antibody Specificity Controls in Vivo Effector Mechanism of Anti-CD20 Reagents, Blood, 103 (2004) 2738-2743.
Craigo, J. K., Montelaro, R. C. Lessons in AIDS vaccine development learned from studies of equine infectious, anemia virus infection and immunity. Viruses 5, 2963-76, (2013).
Crispin et al., "Carbohydrate and domain architecture of an immature antibody glycoform exhibiting enhanced effector functions," *J. Mol. Biol.*, Apr. 17, 2009, 387(5):1061-1066.
Cyranoski, Threat of Pandemic Brings Flu Drug Back to Life, Nat. Med. Sep. 2005, 11(9): 909.
Davies, JW et al., Streamlining Lead Discovery by Aligning in Silico and High-Throughput Screening, Curr Opin Chem Biol. Aug. 2006; 10(4):343-51.
Davodeau et al., "Close phenotypic and functional similarities between human and murine $\alpha\beta$ T cells expressing invariant TCR alpha-chains," *J. Immunol.*, Jun. 15, 1997, 158(12):5603-5611.
Debets, M. F. et al., Bioconjugation with Strained Alkenes and Alkynes, Acc. Chem. Res. 2011, 44, 805-815.
Dejong et al., Fatal outcome of human influenza A (H5N1) is associated with high viral load and hypercytokinemia. Nat Med Oct. 2006;12(10):1203-7. Epub Sep. 10, 2006.
Delente, Jacqubs, Glycosylation Revisited, Trends in Biotechnology 3, letters to editor, No. 9 (1985).
Dellabona et al., "An invariant $V\alpha 24$-$J\alpha Q/V\beta 11$ T cell receptor is expressed in all individuals by clonally expanded $CD4^{-}8^{-}$ T cells," *J. Exp. Med.*, Sep. 1, 1994, 180(3):1171-1176.
Demchenko, A.V., Ed., Hanbook of Chemical Glycosylation: Advances in Stereoselectivity and Therapeutic Relevance (2008) Wiley-VCH. Chapter 1. General Aspects of the Glycosidic Bond Formation, in 28 pages.
Dennis, Carina, Cancer: Off by a whisker, Nature 442: 739-741 (2006).
De Paz, J. L., Horlacher, T. & Seeberger, P.H. Oligosaccharide microarrays to map interactions of carbohydrates in biological systems. Methods Enzymol. 415, 269-292, (2006).
Dhodapkar et al., "$\alpha$-Galactosyl ceramide-loaded dendritic cells for expansion of natural killer T cells" CAPLUS 145:354715 (2006).
Dhodapkar et al., "A reversible defect in natural killer T cell function characterizes the progression of premalignant to malignant multiple myeloma," *J. Exp. Med.*, Jun. 16, 2003, 197(12):1667-1676.

(56) References Cited

OTHER PUBLICATIONS

Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.
Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.
Dommerholt, Jan, Readily Accessible Bicyclononynes for Bioorthogonal Labeling and Three-Dimensional Imaging of Living Cells, Angew. Chem. Int. Ed. 2010, 49, 9422-9425.
Doores KJ, et al. A nonself sugar mimic of the HIV glycan shield shows enhanced antigenicity. Proc. Natl. Acad Sci. US.A. 107(40), 17107-17112, (2010).
Doores, K. J. & Burton, D.R. Variable Loop Glycan Dependency of the Broad and Potent HIV-I-Neutralizing Antibodies PG9 and PG16. J. Virol. 84, 10510-10521, (2010).
Doores, K. J. et al. Envelope glycans of immunodeficiency virions are almost entirely oligomannose antigens. Proc. Natl. Acad. Sci. U.S. A 107, 13800-13805, (2010).
Doronina, Svetlana et al., Development of Potent Monoclonal Antibody Auristatin Conjugates for Cancer Therapy, Nat Biotechnol 21(7): 778-784 (2003).
Dougan, Michael et al., Immune Therapy for Cancer, Annual Review of Immunology, 2009, 27, pp. 83-117.
Drugs of the future 25(7): 686 (2000).
Dubertret. Benoit et al., In Vivo Imaging of Quantum Dots Encapsulated in Phospholipid Micelles, Science 298:759-1762, 2002.
Duncan, AR; Winter, G, The binding Site for C1q on IgG, Nature 322:738-40 (1988).
Dunn et al., Zanamivir: A Review of Its Use in Influenza, Drugs, Oct. 1999, 58(4):761-784.
Eberl et al., "Selective bystander proliferation of memory CD4+ and CD8+ T cells upon NK T or T cell activation," *J. Immunol.*, Oct. 15, 2000, 165(8):4305-4311.
Eberl et al., "Selective induction of NK cell proliferation and cytotoxicity by activated NKT cells," *Eur. J. Immunol.*, Apr. 2000, 30(4):985-992.
Eggink, D. et al. Lack of complex N-glycans on HIV-I envelope glycoproteins preserves protein conformation and entry function. Virology 401, 236-247, (2010).
Eisen, Michael et al., Binding of the Influenza A Virus to Cell-Surface Receptors: Structures of Five Hemagglutinin-Sialyloligosaccharide Complexes Determined By X-Ray Crystallography, Virology, 232:19, 1997.
Ellis J., et al., Evaluation of Four Real-Time PCR Assays for Detection of Influenza A9H1N1)v Viruses, Euro Surveill. 2009; 14(22), p. 1-3.
Evans, Michael et al., "Mechanism-based profiling of enzyme families," *Chem. Rev.*, Aug. 2006, 106(8):3279-3301.
Evans, "The rise of azide-alkyne 1,3-dipolar 'click' cycloaddition and its application to polymer science and surface modification," *Australian J. Chem.*, Jun. 2007, 60(6):384-395.
Falkowska, E. et al. Broadly neutralizing HIV antibodies define a glycan-dependent epitope on the prefusion conformation of gp41 on cleaved envelope trimers Immunity 40, 657-68, 2014.
Fazio, F. et al., Synthesis of sugar arrays in microtiter plate. J. Am. Chem Soc. 124, 14397-14402, (2002).
FDA Guidance for Industry for Container Closure Systems for Packaging Human Drugs and Biologics, May 1999.
Fedson, Confronting the next influenza pandemic with antiinflammatory and immunomodulatory agents: why they are needed and how they might work. Influenza Other Respi Virusts. Jul. 2009;3(4):129-42.
Feizi, Ten, Carbohydrate Differentiation Antigens: Probable Ligands for Cell Adhesion Molecules,Trends Biochem. Sci. 16, 84-86.
Fernandez-Tejada, Alberto et al., Designing synthetic vaccines for HIV. Expert Rev. Vaccines 14, 815-31, 2015.
Fernandez-Megia et al., A Click Approach to Unprotected Glycodendrimers. Macromolecules 2006, vol. 39, pp. 2113-2120.

Fessner et al., Enzymes in Organic Synthesis, Short Enzymatic Synthesis of L-Fucose Analogs. Eur. J. Org. Chem 2000, p. 125-132.
Fiehn, Oliver, Combining Genomics, Metabolome Analysis, and Biochemical Modelling to Understand Metabolic Networks, Comparative and Functional Genomics 2:155-168, 2001.
Fraker, PJ et al., Protein and Cell Membrane Iodination with a Sparingly Soluble Chloroamide, 1,3,4,6-tetrachloro-3a,6a-diphrenylglycoluril, Biochem. Biophys. Res. Commun. 80: 49-57 (1978).
Friscourt, F. et al., A Fluorogenic Probe for the Catalyst-Free Detection of Azide-Tagged Molecules, J. Am. Chem. Soc. 2012, 134, 18809-18815.
Fujimore, Kenji et al., A Modeling Analysis of Monoclonal Antibody Percolation Through Tumors: A Binding-Site Barrier, J Nuc Med. 31: 1191-1198 (1990).
Fujio, M. et al. "Structure-Based Discovery of Glycolipids for CD1d-Mediated NKT Cell Activation: Turning the Adjuvant versus Immunosuppression Activity." CAPLUS 145:240945 (2006).
Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.
Fukui, S et al., Oligosaccharide microarrays for high-throughput detection and specificity assignments of carbohydrate-protein interactions. Nat. Biotechnol. 20, 1011-1017, (2002).
Gabius, HJ. Tumor Lectinology: at the intersection of carbohydrate chemistry, biochemistry, cell biology and oncology. Angew. Chem. Int. Ed. Engl. 27, 1267-1276.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
Geiler et al., Comparison of pro-inflammatory cytokine expression and cellular signal transduction in human macrophages infected with different influenza A viruses. Med Microbiol Immunol. Feb. 2011;200(1):53-60.
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins Via Periodate Oxidation of a 2-amino Alcohol. Applications to Modification at N-Terminal Serine, Bioconjugate chem. 3:138-146 (1992).
Giaccone, Giuseppe et al., "A phase I study of the natural killer T-cell ligand α-galactosylceramide (KRN7000) in patients with solid tumors," *Clin. Cancer Res.*, Dec. 2002, 8(12):3702-3709.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun. 2005, 73, 4803.
Goldenthal et al., "Safety Evaluation of Vaccine Adjuvants: National Cooperative Vaccine Development Working Group," *AIDS Res. Hum. Retroviruses*, 1993, 9(Supp. 1):S47-S51.
Govorkova et al, Combination chemotherapy for influenza. Viruses. Aug. 2010;2(8): 1510-29.
Graham, Duncan et al., Surface-Enhanced Resonance Raman Scattering as a Novel Method of DNA Discrimination, Angew. Chem., 2000, 112(6), 1103-1105.
Grandjean, C. et al., On The Preparation of Carbohydrate-Protein Conjugates Using the Traceless Staudinger Ligation, J Org Chem 2005, 70, 7123-7132.
Greenbaum et al., "Chemical approaches for functionally probing the proteome," *Mol. Cell. Proteomies*, 2002, 1:60-68.

(56) References Cited

OTHER PUBLICATIONS

Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.
Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.
Gulland, Fire Cases of Spread of Oseltamivir Resistant Swine Flu Between Patients are Reported in Wales, BMJ, Nov. 23, 2009:339:b4975.
Ha, Ya et al., X-Ray Structures of H5 Avian and H9 Swine Influenza Virus Hemagglutinins Bound to Avian and Human Receptor Analogs, Proc Natl Acad Sci USA, 98:11181-11186, 2001.
Ha, Ya et al., X-Ray Structure of the Hemagglutinin of a Potential H3 Avian Progenitor of the 1968 Hong Kong Pandemic Influenza Virus, Virology, 309:209-218, 2003.
Hajishengallis, "Mucosal immunization with a bacterial protein antigen genetically coupled to cholera toxin A2/B subunits,"*J. Immuol.*, May 1, 1995, 154(9):4322-4332.
Ham, Richard et al., Media and Growth Requirements, Meth. Enz 58, 44 (1979).
Hammerling et al., in: Monoclonal Antibodies and T-Cell Hybridomas 563-587, 1981.
Han, Junyan et al., 3- and 5-Functionalized BODIPYs via the Liebeskind-Srogl Reaction, Organic & Biomolecular Chemistry (2009), 7(1), 34-36.
Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).
Hasegawa, Akira, et al., Synthesis of Sialyl Lewis X Ganglioside Analogues Containing Modified L-Fucose Residues, Carbohydr. Res. 1995, 274, 165-181.
Hata, K. et al., Limited Inhibitory Effects of Oseltamivir and Zanamivir on Human Sialidases, Antimicrobial Agents and Chemotherapy, vol. 52, No. 10, Oct. 2008, in 8 pages.
Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.
Henglein, A. et al., Absorption Spectrum and Some Chemical Reactions of Colloidal Platinum in Aqueous Solution, J. Phys. Chem., 99, 14129 (1995).
Herner, A et al., A new family of bioorthogonally applicable fluorogenic labelst, Org. Biomol. Chem. 2013, 11, 3297-3306.
Hey, Thomas et al., Artificial, non-antibody binding proteins for pharmaceutical and industrial application, Trends in Biotechnology 23(10) 514-522 (2005).
Himbayashi, J. et al., Oligosaccharide Microarrays for Glycomics, Trends in Biotechnology 21 (4): 141-143, 2003.
Holmskov, Uffe et al., Collectins: Collagenous C-Type Lectins of the Innate Immune Defense System, 1994, Immunol. Today, 15: 67.
Honda et al., Synthesis and anti-influenza virus activity of 7-0-alkylated derivatives related to zanamivir. Bioorg Med Chem Lett. Aug. 5, 2002;12(15):1925-8.
Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," *Immunol. Today*, Jun. 1992, 13(6):198-200.
Hsu et al., "Alkynyl sugar analogs for the labeling and visualization of glycoconjugates in cells," *Proc. Natl. Acad. Sci. USA*, Feb. 20, 2007, 104(8), 2614-2619.
Hsu, C, H. et al. Highly alpha-selective sialyl phosphate donors for efficient preparation of natural sialosides. Chem. Eur. J 16-6, 1754-1760, (2010).
Huang, Lijun et al., Iterative One-Pot Syntheses of Chitotetroses, Carbohydr. Res. 2006, 341, 1669-1679.
Huang et al., Recombinant immunotherpaeutics: current state and perspectives regarding the feasibility and market, Appl Microbiol Biotechnol, 87: 401-410. 2010.
Immunogenicity, Wikipedia p. 1-3. Downloaded on Aug. 16, 2016 from https://en.wikipedia.org/wild/Immunogenicity. (2016).
International Search Report and Written Opinion issued for International application No. PCT/US2015/011748, dated Aug. 21, 2015, 17 pages.
International Search Report dated Jan. 13, 2012, from corresponding International Patent Application No. PCT/US2011/035982, 17 pages.
International Search Report dated Nov. 13, 2014, from corresponding International Patent Application No. PCT/US2014/054617, 10 pages.
International Search Report and Written Opinion in International Application No. PCT/US16/15858, dated Jun. 27, 2016, in 8 pages.
International Search Report issued for International application No. PCT/US2009/050754, dated Feb. 24, 2010, 10 pages.
International Search Report and Written Opinion in International Application No. PCT/US2017/021454, dated Jul. 31, 2017, 8 pages.
Isshiki et al., Cloning, Expression, and Characterization of a Novel UDP-galactose:b-N-Acetylglucosamine b1,3-Galactosyltransferase (b3Gal-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihiro et al., A Novel Ganglioside Isolated From Renal Cell Carcinoma, Biol Chem 2001, 276, 16695.
Jacobs et al., "Metabolic labeling of glycoproteins with chemical tags through unnatural sialic acid biosynthesis," *Methods Enzymol.*, 2000, 327:260-275.
Japanese Office Action Dated Apr. 21, 2015, from Related Japanese Patent Application No. 2013-510261, 6 Pages.
Jayasena, Sumedha, Aptamers: An Emerging Class of Molecules That Rival Antibodies in Diagnostics, Clin. Chem. (1999), 45, 1628-1650.
Jewett, J.C.; Bertozzi, C.R., Cu-Free Click Cycloaddition Reactions in Chemical Biology, Chem. Soc. Rev. 2010, 39, 1272-1279.
Jewett, J.C.; Sletten, E. M.; Bertozzi, Cr., Rapid Cu-Free Click Chemistry with Readily Synthesized Biarylazacyclooctynones, J. Am. Chem. Soc. 2010, 132, 3688-3690.
Jin, R. C. et al., Photoinduced Conversion of Silver Nanospheres to Nanoprisms, Science (2001), 294, 1901-1903.
Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.
John, F. & Hendrickson, T. L. Synthesis of Truncated Analogues for Studying the Process of Glycosyl Phosphatidylinositol Modification. Org. Lett. 12, 2080-2083, (2010).
Jonges, M. et al., Dynamics of Antiviral-Resistant Influenza Viruses in the Netherlands, 2005-2008, Antiviral Res., Sep. 2009, 83(3): 290-297.
Jorgensen, Trond et al., Up-Regulation of the Oligosaccharide Sialyl Lewisx: A New Prognostic Parameter in Metastatic Prostate Cancer, Cancer Res. 55, 1817-1819, 1995.
Jose, Jiney et al., Energy transfer dyads based on Nile Red, Tetrahedron Letters (2009), 50(47), 6442-6445.
Joshi, Shantaran et al., Cell Surface Properties Associated with Malignancy of Metastatic Large Cell Lymphoma Cells, (1987) Cancer Res. 47, 3551-3557.
Joyce, J. G. et al. An oligosaccharide-based HIV-I 2Gl2 mimotope vaccine induces carbohydrate-specific antibodies that fail to neutralize HIV-I virions. Proc. Natl. Acad. Sci. U. S. A 105, 15684-15689, (2008).

(56) References Cited

OTHER PUBLICATIONS

Kakeji, Y. et al., Correlation Between Sialyl Tn Antigen and Lymphatic Metastasis in Patients with Borrmann Type IV Gastric Carcinoma, Brit. J. Cancer 71, 191-195, 1995.

Kale et al., Detection of intact influenza viruses using biotinylated biantennary S-sialosides. J Am Chem Soc. Jul. 2, 2008;130(26):8169-71.

Kalesh et al., "Peptide-based activity-based probes (ABPs) for target-specific profiling of protein tyrosine phosphatases (PTPs)," Chem. Commun., Jan. 28, 2010, 46(4):589-591.

Kamkaew, A. et al., "BODIPY dyes in photodynamic therapy." Chem. Soc. Rev. 2013, 42, 77-88.

Kawakami et al., "Critical role of V$\alpha$14$^+$ natural killer T cells in the innate phase of host protection against Streptococcus pneumoniae infection," Eur. J. Immunol., Dec. 2003, 33(12):3322-3330.

Kawano et al., "CD1d-restricted and TCR-mediated activation of v$_\alpha$14 NKT cells by glycosylceramides," Science, Nov. 28, 1997, 278(5343):1626-1629.

Kanie, Osman et al., Orthogonal glycosylation strategy in synthesis of extended blood group B determinant. Tetrahedron Lett. 37, 4551-4554 (1996).

Kannappan, Ramaswamy et al., "Photoaffinity labeling of sialidase with a biotin-conjugated phenylaminodizairine derivative of 2,3-didehydro-2-deoxy-N-acetylneuraminic acid," Biol. Pharm. Bull., Mar. 2008, 31(3):352-356.

Karlin, Samuel et al., Applications and Statistics for Multiple High-Scoring Segments in Molecular Sequences, Proc. Natl. Acad Sci. USA 90:5873-77, 1993.

Karmakar, M. et al., Current Trends in Research and Application of Microbial Cellulases, Research Journal of Microbiology, (2001) 6(1): 41-53.

Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).

Kidd et al., "Profiling serine hydrolase activities in complex proteomes," Biochemistry, Apr. 3, 2001, 40(13):4005-4015.

Kiick, K.L. et al., Identificationof an Expanded Set of Translationally Active Methionine Analogues in Escherichia coli, tetrahedron 56:9487, 2001.

Kim et al., High-Throughput Screening of Glycan-Binding Proteins Using Miniature Pig Kidney N-Glycan-Immobilized Beads, Chemistry & biology 15.3, p. 215-223 (2008).

Kim, Gap-Sue et al., AB Initio Study of Excited Electronic States and Vibronic Spectra of Phenyl Radical, Chem Phys. Lett, 2002, 3 5 2, 421.

Kimura et al., Design and Synthesis of Immobilized Tamiflu Analog on Resin for Affinity Chromatography, Tetrahedron Lett., Jul. 1, 2009, 50(26):3205-3208.

King, M. et al., New Tetramethlthiepinium (TMTI) for Copper-Free Click Chemistry, Chem. Commun. 2012, 48, 9308-9309.

Kitamura et al., "$\alpha$-galactosylceramide induces early B-cell activation through IL-4 production by NKT cells," Cell. Immunol., Jan. 10, 2000, 199(1):37-42.

Klein, J. et al., "Isomaltines and their N-acyl derivatives, their preparation, and use of some acyl derivatives as surfactants or for preparation of hydrophilic polymers," CAPLUS 110:95711 (1989).

Kolb et al., "Click chemistry: diverse chemical function from a few good reactions," Angew. Chem. Int. Ed. Engl., Jun. 1, 2001, 40(11):2004-2021.

Kolb et al., "The growing impact of click chemistry on drug discovery," Drug Discov. Today, Dec. 15, 2003, 8(24):1128-1137.

Komba S, et al Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.

Komori, Tatsuya et al., Study on Systematizing the Synthesis of the A-Series Ganglioside Glycans GT1a, GD1a, and GM1 Using the Newly Developed N-Troc-Protected GM3 and GaIN Intermediates, Carbohydr. Res. 2009, 344, 1453.

Kong, L. et al. Expression-system-dependent modulation of HIV-I envelope glycoprotein antigenicity and immunogenicity. J. Mol. Biol. 403, 131-147, (2010).

Kos, "Regulation of adaptive immunity by natural killer cells," Immunol. Res., 1998, 17(3):303-312.

Koshihara et al., 1984, Biochmica et biophysica acta, 792(1), pp. 92-97.

Kotteas et al., Immunotherapy for pancreatic cancer, J cancer Res Clin Oncol, 142(8): 1795-1805, 2016.

Krise, Jeffrey et al., Prodrugs of Phosphates, Phosphonates, and Phosphinates, Adv. Drug Deliv. Rev. 1996, 19(2), 287-310.

Kruis et al., Low dose balsalazide (1.5 g twice daily) and mesalazine (0.5 g three times daily) maintained remission of ulcerative colitis but high dose alsalazide (3.0 g twice daily) was superior in preventing relapses. Gut. Dec. 2001;49(6):783-9.

Kubin, R. F. et al., Fluorescence Quantum Yields of Some Rhodamine Dyes, Luminescence 1982, 27, 455-462.

Kubler-Kielb, J. et al., A New Method for Conjugation of Carbohydrates to Proteins Using an Aminooxy-Thiol Heterbifunctional Linker, J Org Chem 2005, 70, 6987-6990.

Kwong, Peter et al., Rational Design of Vaccines to Elicit Broadly Neutralizing Antibodies to HIV-I. Cold Spring Harb.Perspect. Med. 1, 2011, 1-16.

Lantz et al., "An invariant T cell receptor $\alpha$ chain is used by a unique subset of major histocompatibility complex class I-specific CD4$^+$ and CD4$^-$8$^-$ T cells in mice and humans," J. Exp. Med., Sep. 1, 1994, 180(3):1097-1106.

Lau, K. et al. Highly efficient chemoenzymatic synthesis of $\beta$1-4-linked galactosides with promiscuous bacterial $\beta$1-4-galactosyltransferases. Chem. Commun. 46, 6066-6068, (2010).

Le, Mai et al., Avian flu: Isolation of Drug-Resistant H5N1 Virus, Nature, Oct. 20, 2005, 437(7062):1108.

Lebens et al., Mucosal vaccines based on the use of cholera toxin B as immunogen and antigen carrier, Dev. Biol. Stand., 1994, 82:215-227.

Le Droumaguet, C. et al., Fluorogenic Click Reaction., Chem. Soc. Rev. 2010, 39, 1233-1239.

Lederman et al., A single amino acid substitution in a common African allele of the CD4 molecule ablates binding of the monoclonal antibody, OKT4, Molecular Immunology, 28, 1171-1181 (1991).

Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.

Lee et al., A new Solvent System for Efficient Synthesis of 1,2,3-Triazoles, Tetrahedron Lett., Jul. 17, 2006, 47(29):5105-5109.

Lee et al., An Efficient and Practical Method for the Synthesis of Mono-N-Protected $\alpha,\omega$-diaminoalkanes, Tetrahedron Lett., Apr. 2, 2001, 42(14):2709-2711.

Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004.

Lee et al., Immunogenicity Study of Globo H Analogues with Modification at the Reducing or Nonreducing end of the tumor antigen, J Am Chem Soc, 136: 16844-16853 (2014).

Lemieux, R. U. et al., Halide ion catalyzed glycosidation reactions. Syntheses of a-linked disaccharides. J Am. Chem. Soc. 97(14), 4056-62, (1975).

Lew et al., Discovery and Development of GS 4104 (oseltamivir): an Orally Active Influenza Neuraminidase Inhibitor, Curr Med Chem, Jun. 2000, 7(6):663-672.

Li et al., $\beta$-endorphin omission analogs: Dissociation of Immunoreactivity from other biological activities, Proc Natl Avad Sci USA, 77:3211-3214 (1980).

Li, Y. L. et al., Crystallization and Melting Behaviors of PPC-BS/ PVA Blends, 19, 1557-1566, 2003.

Li, Henghui et al., MALDI-MS Analysis of Sialylated N-Glycan Linkage Isomers Using Solid-Phase Two Step Derivatization Method, Analytica Chimica Acta 924 (2016) 77-85.

(56) References Cited

OTHER PUBLICATIONS

Li et al., "Design of a potent CD1d-binding NKT cell ligand as a vaccine adjuvant," *Proc. Natl. Acad. Sci. USA*, Jul. 20, 2010, 107:13010-13015.
Li, J.; Hu, M.; Yao, S. Q. "Rapid synthesis, screening, and identification ofxanthone and xanthene-based fluorophores using click chemistry." Org. Lett. 2009, 11, 3008-3011.
Li, Lingling, et al., "Syntheses and spectral properties of functionalized, water-soluble BODIPY derivatives." J. Org. Chem. 2008, 73, 1963-1970.
Li, L. et al. Efficient chemoenzymaUc synthesis of an N-glycan isomer library. Chem. Sci. 6, 5652-5661 (2015).
Liang et al., "Quantitative microarray analysis of intact glycolipid-CD1d interaction and correlation with cell-based cytokine production," *J. Am. Chem. Soc.*, Sep. 17, 2008, 130(37):12348-12354.
Liang, Chi-Hui et al., Iron Oxide/Gold Core/Shell Nanoparticles for Ultrasensitive Detection of Carbohydrate-Protein Interactions, Anal. Chem. 2009; 81, 7750-7756.
Liang, P.H. et al., Quantitative Analysis of Carbohydrate-Protein Interactions Using Glycan Microarrays: Determination of Surface and Solution Dissociation Constants, J. Amer. Chem. Sci. 2007, 129, 11177-11184.
Liu et al., "Activity-based protein profiling: the serine hydrolases," *Proc. Natl. Acad. Sci. USA*, Dec. 21, 1999, 96(26):14694-14699.
Liu et al., Enhanced anti-influenza agents conjugated with anti-inflammatory activity. J Med Chem. Oct. 11, 2012;55(19):8493-501.
Liu et al., Intramolecular ion-pair prodrugs of znamivir nad guanidino-oseltamivir. Bioorganic & Medicinal Chemistry. Jun. 2011; 19(16):4796-4802.
Liu et al., Synthesis and anti-influenza activities of carboxyl alkoxyalkyl esters of 4-guanidino-Neu5Ac2en (zanamivir) Bioorg Med Chem Lett. Sep. 1, 2007;17(17):4851-4. Epub Jun. 20, 2007.
Lopes, J.F. et al., Simulataneous Chromatographic Separation of Enantiomers, Anomers and Structural Isomers of Some Biologically Relevant Monsaccharides. J. Chomatogr. A, (2008) 1188:34-42.
Lou, et al., Stage-specific embryonic antigent-4 as a potential therapeutic target in glioblastoma multiforms and other cancers. Proc Natl Acad Sci USA 2014, 111(7):2482-7.
Loudet, A.; Burgess, K. "BODIPY dyes and their derivatives: syntheses and spectroscopic properties." Chem. Rev. 2007, 107, 4891-4932.
Lu et al., "Design of a mechanism-based probe for neuraminidase to capture influenza viruses," *Angew. Chem. Int. Ed. Engl.*, Oct. 28, 2005, 44(42):6888-6892.
Lu, Guokai et al., Reactivity-Based One-Pot Synthesis of Immunosuppressive Glycolipids From the Caribbean Sponge Plakortis Simplex, J. Chem. 2009, 27, 2217-2222.
MacBeath, G. and Schreiber, S. L., Printing Proteins as Microarrays for High-Throughput Function Determination, Science, 289, 1760-1763, 2000.
Makino et al., Predominant expression of invariant $V_\alpha 14^+$ TCR α chain in $NK1.1^+$ T cell populations, *Int. Immunol.*, Jul. 1995, 7(7):1157-1161.
Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).
Marcato et al., "Chapter 17: The Rocky Road from Cancer Stem Cell Discovery to Diagnostic Applicability," Cancer Stem Cells Theories and Practice, pp. 335-360, Mar. 22, 2011.
Massart, R , IEEE Transactions on Magnetics, 17, 1247 (1981).
Masuko, T. et al., Thiolation of Chitosan. Attachment of Proteins Via Thioether Formation, Biomacromolecules 2005, 6, 880-884.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matz et al., "Fluorescent proteins from nonbioluminescent Anthozoa species," *Nat. Biotechnol.*, Oct. 1999, 17(10):969-973.

McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.
Medelson et al., NKp46 O-glycan Sequences that are involved in the interaction with Hemagglutinin Type 1 of Influenza Virus. J. Virol. Feb. 10, 2010, 84(8):3789-3797.
McLellan, J. S. et al. Structure of HIV-I gpl20 V1/V2 domain with broadly neutralizing antibody PG9. Nature 480, 336-343, 2011.
Milstein, C & Cuello, AC, Hybrid Hydridomas and their use in immunohistochemistry, Nature 305, 537-540, Oct. 1993.
Miyagi et al., "Mammalian sialidases: Physiological and pathological roles in cellular functions," *Glycobiology*, Jul. 2012, 22(7):880-896.
Miyagi et al., "Plasma membrane-associated sialidase as a crucial regulator of transmembrane signalling," *J. Biochem.*, Sep. 2008, 144(3):279-285.
Miyagi et al., "Sialidase and malignancy: a minireview," *Glycoconj. J.*, 2004, 20(3):189-198.
Miyagi, "Aberrant expression of sialidase and cancer progression," *Proc. Jpn. Acad. Ser. B. Phys. Biol. Sci.*, 2008(10), 84:407-418.
Miyaji, E. N. et al., Induction of Neutralizing Antibodies Against Diphtheria Toxin by Priming with Recombinant Mycobacterium Bovis BCG Expressing CRM197, a Mutant Diphtheria Toxin, Infect. Inunun. 2001, 69, 869.
Miyamoto et al., "A synthetic glycolipid prevents autoimmune encephalomyelitis by inducing $T_H 2$ bias of natural killer T cells," *Nature*, Oct. 4, 2001, 413(6855):531-534.
Monti et al., "Sialidases in vertebrates: a family of enzymes tailored for several cell functions," *Adv. Carbohydr. Chem. Biochem.*, 2010, 64:403-479.
Moody, M. D. et al., Array-based ELISAs for High-Throughput Analysis of Human Cytokines. Biotechniques (2001), 31, 186-194.
Morphy et al., Designed multiple ligands. An emerging drug discovery paradigm. J Med Chem. Oct. 20, 2005;48(20:6523-43.
Morphy et al., From magic bullets to designed multiple ligands. Drug Discov Today. Aug. 1, 2004;9(15):641-51.
Moscona, "Global transmission of oseltamivir-resistant influenza," N Engl. J Med, Mar. 5, 2009, 360(10):953-956.
Moscona, Oseltamivir Resistance—Disabling Our Influenza Defenses, The New England Journal of Medicine, 2005, vol. 353, pp. 2633-2636.
Mosmann et al., "The expanding universe of T-cell subsets: Th1, Th2 and more," *Immunol. Today*, Mar. 1996, 17(3):138-146.
Mossong et al., "Emergence of oseltamivir-resistant influenza A H1N1 virus during the 2007-2008 winter season in Luxembourg: clinical characteristics and epidemiology," Antiviral Res., Oct. 2009, 84(1):91-94.
Mouquet, H. et al. Complex-type N-glycan recognition by potent broadly neutralizing HIV antibodies. Proc. Natl. Acad. Sci. U. S. A 109, E3268-E3277, (2012).
Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).
Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).
Natarajan et al, Caffeic acid phenethyl ester is a potent and specific inhibitor of activation of nuclear transcription factor NF-kappa B. Proc Natl Acad Sci USA Aug. 20, 1996;93(17):9090-5.
Ni, Jing et al., Immunoassay Readout Method Using Extrinsic Raman Labels Adsorbed on Immunogold Colloids, Anal. Chem., 1999, 71(21), pp. 4903-4908.

(56) References Cited

OTHER PUBLICATIONS

Nieuwenhuis et al., "CD1d-dependent macrophage-mediated clearance of *Pseudomonas aeruginosa* from lung," Nat. Med., Jun. 2002, 8(6):588-593.
Nielsen, U. B. et al., Multiplexed Sandwich Assays in Microarray Format, Journal Immunol. Meth. (2004), 290, 107-120.
Ning, X. et al., Visualizing Metabolically-Labeled Glycoconjugates of Living Cells by Copper-Free and Fast Huisgen Cycloadditions, J. Angew. Chem. Int. Ed. 2008, 47, 2253 -2255.
Nowak, MW et al., Nicotinic Receptor Binding Site Probed With Unnatural Amino Acid Incorporation in Intact Cells, Science 268:439, 1995.
Novotny et al., "Structural invariants of antigen binding: comparison of immunoglobulin $V_L$-$V_H$ and $V_L$-$V_L$ domain dimers," Proc. Natl. Acad. Sci. USA, Jul. 1985, 82(14):4592-4596.
Office Action dated Dec. 3, 2013, from corresponding Chinese Patent Application No. 201180034218.3, 15 total pages.
Office Action dated Oct. 22, 2014, from corresponding Chinese Patent Application No. 201180034218.3, 16 total pages.
O'Garra, "Cytokines induce the development of functionally heterogeneous T helper cell subsets," Immunity, Mar. 1998, 8(3):275-283.
Okada, Yoshio et al. Changes in the Expression of Sialyl-Lewisx, a Hepatic Necroinflammation-Associated Carbohydmte Neoantigen, in Human Depatocellular Carcinomas, (1994) Cancer 73, 1811-1816.
Okamura et al., "Interleukin-18: a novel cytokine that augments both innate and acquired immunity "Adv. Immunol., 1998, 70:281-312.
Olden, Kenneth et al., Carbohydrate Moieties of Glycoproteins: A Re-Evaluation of Their Function, Biochem et Biophys Acta 650:209-232 (1982).
Otsubo N, et al., An Efficient and Straightforward Synthesis of Sialyl Lex Glycolipid as a Potent Selectin Blocker[[1]], Carbohydr. Res. 1998, 306, 517-530.
Ottolini et al., Combination anti-inflammatory and antiviral therapy of influenza in a cotton rat model. Pediatr. Pulmonol. 2003:36;290-4.
Oyelaran, 0. & Gildersleeve, J. C. Glycan arrays: recent advances and future challenges. Curr. Opin. Chem. Biol. 13, 406-413, (2009).
Pabst, M. et al., Glycan profiles of the 27 Nglycosylation sites of the HIV envelope protein CN54gp140. Biol. Chem. 393, 719-730, (2012).
Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.
Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).
Pancera, M. et al. Structural basis for diverse N-glycan recognition by HIV-I-neutralizing V1-V2-directed antibody PG16. Nat. Struct. Mol. Biol. 20, 804-813, (2013).
Parker, C. A.; Rees, W. T., Correction of Fluorescence Spectra and Measurement of Fluorescence Quantum Efficiency, Analyst 1960, 85, 587-600.
Parrish, M. L. et al., A Microarray Platform Comparison for Neuroscience Applications, J. Neurosci. Methods, 2004, 132, 57-68.
Patricelli et al., "Functional interrogation of the kinome using nucleotide acyl phosphates," Biochemistry, Jan. 16, 2007, 46(2):350-358.
Paulson, J. C., Blixt, 0. & Collins, B. E. Sweet spots in functional glycomics. Nat. Chem. Biol. 2, 238-248, (2006).
Peelle et al., "Characterization and use of green fluorescent proteins from *Renilla mulleri* and *Ptilosarcus guernyi* for the human cell display of functional peptides," J. Protein Chem., Aug. 2001, 20(6):507-519.
Peiris et al., Re-emergence of fatal human influenza A subtype H5Nldisease. Lancet. Feb. 21, 2004 ;363(9409):617-9.

Pejchal, R. et al. A potent and broad neutralizing antibody recognizes and penetrates the HIV glycan shield. Science 334, 1097-1103, (2011).
Pellicci et al., "Differential recognition of CD1d-α-galactosyl ceramide by the Vβ8.2 and Vβ7 semi-invariant NKT T-cell receptors," Immunity, Jul. 17, 2009, 31(1):47-59.
Perlmutter, R.M. et al., Subclass Restriction of Murine Anti-Carbohydrate Antibodies, Journal of Immunology 1978, 121, 566-572.
Pettit, George et al., Antineoplastic Agents. Part 189. The Absolute Configuration and Synthesis of Natural (−)-Dolastatin 10, J Am Chem Soc. 111:5463-5465 (1989).
Pettit, George et al., Dolastatins 23: Stereospecific Synthesis of Dolaisoleuine, J Chem Soc Perkin Trans. 15:853-858 (1996).
Pettit, George et al., Antineoplastic Agents 365. Dolastatin 10 SAR Probes, Anti-Cancer Drug Design 13:243-277 (1998).
Pettit, Robin et al., Specific Activities of Dolastatin 10 and Peptide Derivatives Against Cryptococcus Neoformans, Antimicrob Agents Chemother. 42:2961-2965 (1998).
Pettit, George et al., The Dolastatins; 18: Stereospecific Synthesis of Dolaproine, Synthesis, 719-725 (1996).
Piizi, G. and Hardinger, S., Stereochemistry: an Introduction, UCLA Chemistry 30A Presentation, Fall 2002, in 40 pages.
Porcelli, S.A., "Preparation of α-galactosylceramide derivatives as modulators of immunity and autoimmunity," CAPLUS 147:440317 (2007).
Potter et al., "Fluorometric assay of neuraminidase with a sodium (4-methylumbelliferyl-alpha-D-N-acetylneuraminate) substrate," Anal. Biochem., Apr. 15, 1979, 94(2):287-296.
Pratt, M. R. & Bertozzi, C. R. Chemoselective ligation applied to the synthesis of a biantennary N-linked glycoform of CD52. J Am. Chem. Soc. 125, 6149-6159, (2003).
Prescher, J. A.; Bertozzi, C.R. "Chemistry in living systems." Nat. Chem. Biol. 2005, 1, 13-21.
Pritchard, L. K. et al. Structural Constraints Determine the Glycosylation of HIV-I Envelope Trimers. Cell Rep. 11, 1604-13, (2015).
Pritchard, Laura et al., Cell- and Protein- Directed Glycosylation of Native Cleaved HIV-I Envelope. J. Virol. 89, 8932-44, (2015).
Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosoinal catabolism of keratan sulfate.
Qi, Jianjun et al., Developing visible fluorogenic 'clickon' dyes for cellular imaging, Bioconjugate Chem. 2011, 22, 1758-1762.
Rabbani, Said et al., Glycosyltransferases: An efficient tool for the enzymatic synthesis of oligosaccharides and derivatives as well as mimetics thereof Chimia 60, 23-27, (2006).
Ran et al., "Synthesis and evaluation of 3'- and 4'-deoxy and -fluoro analogs of the immunostimulatory glycolipid, KRN7000," Bioorg. Med. Chem. Lett., 2009, 19:4122-4125.
Rana, G. Kucukayan-Dogu, E. Bengu "Growth of vertically aligned carbon nanotubes over self-ordered nano-porous alumina films and their surface properties" Applied Surface Science, 2012, 258 7112-7117.
Raska, M. et al. Glycosylation patterns of HIV-I gpl20 depend on the type of expressing cells and affect antibody recognition. J. Biol. Chem. 285, 20860-20869, (2010).
Rillahan, C. D. & Paulson, J. C. Glycan microarrays for decoding the glycome. Annu. Rev. Biochem. 80, 797-823, (2011).
Ritamo, Ilja al., Comparison of the Glycosylation of in Vitro Generated Polyclonal Human lgG and Therapeutic Immunoglins, Mol Immunol. Feb. 2014; 57(2): 255-62.
Rogers, GN et al., Single Amino Acid Substitutions in Influenza Haemagglutinin Change Receptor Binding Specificity. Nature, 304:76, 1983.
Rogers, GN et al., Receptor Determinants of Human and Animal Influenza Virus Isolates: Differences in Receptor Specificity of the H3 Hemagglutinin Based on Species of Origin. Virology, 127:361, 1983.
Romagnani, "Induction of $T_H 1$ and $T_H 2$ responses: a key role for the 'natural' immune response?" Immunol. Today, Oct. 1992, 13(10):379-381.

(56) References Cited

OTHER PUBLICATIONS

Rosenstein, N. E. et al, Meningococcal Disease, N Engl J Med 2001, 344, 1378-1388.
Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.
Roth, Jurgen et al., Reexpression of Poly(sialic Acid) Units of the Neural Cell Adhesion Molecule in Wilms Tumor, Proc. Natl. Acad. Sci. 85, 2999-3000, 1988.
Rudnick et al., Affinity and Avidity in Antibody-Based Tumor Targeting, Can Biotherp & Radoipharm, 24, 155-162 (2009).
Russell et al., "The structure of H5N1 avian influenza neuraminidase suggests new opportunities for drug design," Nature, Sep. 7, 2006, 443(7107):45-49.
Saito, Seiichi et al., Haptoglobin-β Chain Defined by Monoclonal Antibody RM2 as a Novel Serum Marker for Prostate Cancer, Int. J Cancer, 2008, 123(3), 633-640.
Saitoh, Osamu et al., Differential Glycosylation and Cell Surface Expression of Lysosomal Membrane Glycoproteins in Sublines of a Human Colon Cancer Exhibiting Distinct Metastatic Potentials*, J. Biol. Chem. 267, 5700-5711, 1992.
Salisbury et al., "Activity-based probes for proteomic profiling of histone deacetylase complexes," *Proc. Natl. Acad. Sci. USA*, Jan. 23, 2007, 104(4):1171-1176.
Salomon et al., Inhibition of the cytokine response does not protect against lethal H5N1 nfluenza infection. Proc Natl Acad Sci U S A Jul. 24, 2007;104(30): 12479-81.
Sarna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).
Sarkar et al., "Disaccharide uptake and priming in animal cells: inhibition of sialyl Lewis X by acetylated Galβ1→4GlcNAcβ-O-naphthalenemethanol," *Proc. Natl. Acad. Sci. USA*, Apr. 11, 1995, 92(8):3323-3327.
Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.
Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. USA., 2006, 103, 12371-12376.
Sawada, Tetsuji et al., E-Selectin Binding by Pancreatic Tumor Cells is Inhibited by Cancer Sera, Int. J. Cancer 57, 901-907, 1994.
Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.
Scanlan, C. N. et al., Exploiting the defensive sugars of HIV-I for drug and vaccine design. Nature 446, 1038-1045, (2007).
Schena, M. et al Quantitative Monitoring of Gene Expression Patterns with a Complementary DNA Microarray, Science, 1995, 270:467-70.
Schengrund et al., "Localization of sialidase in the plasma membrane of rat liver cells," *J. Biol. Chem.*, May 10, 1972, 247(9):2742-2746.
Schmitz, U. et al., Phage Display: A Molecular Tool for the Generation of Antibodies—A Review, Placenta, 21 Suppl. A:S 106 (2000).
Schneider, M.C. et al., Interactions Between Neisseria Meningitidis and the Complement System, Trends Microbial 2007, 15, 233-240.
Schroder et al., The Peptides, vol. 1, p. 76-136, 1965.
Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.
Schweitzer, Barry et al., Multiplexed Protein Profiling on Microarrays by Rolling-Circle Amplification, Nat. Biotechnol. (2002), 20, 359-365.
Scurr, D. J. et al. Surface characterization of carbohydrate microarrays. Langmuir 26, 17143-17155, (2010).
Serna, S. et al., Construction of N-Glycan Microarrays by Using Modular Synthesis and On-Chip Nanoscale Enzymatic Glycosylation. Chem. Eur. J 16, 13163-13175, (2010).
Severi et al., "Sialic acid utilization by bacterial pathogens," *Microbiology*, Sep. 2007, 153(Pt 9):2817-2822.
Seyrantepe et al., "Neu4, a novel human lysosomal lumen sialidase, confers normal phenotype to sialidosis and galactosialidosis cells," *J. Biol. Chem.*, Aug. 27, 2004, 279(35):37021-37029.
Sheu et al., "Surveillance for neuraminidase inhibitor resistance among human influenza A and B viruses circulating worldwide from 2004 to 2008," *Antimicrob. Agents Chemother.*, Sep. 2008, 52(9):3284-3292.
Shie, Jiun-Jie et al., "A concise and flexible synthesis of the potent anti-influenza agents tamiflu and tamiphosphor," Angew. Chem. Int. Ed Engl., 2008, 47(31):5788-5791.
Shie, Jiun-Jie et al., An Azido-BODIPY Probe for Glycosylation: Initiation of Strong Fluorescence Upon Triazole Formation, J. Am. Chem. Soc. 2014, 136, 9953-9961.
Shieh, Peyton et al., Fluorogenic Azidofluoresceins for Biological Imaging, J. Am. Chem. Soc. 2012, 134, 17428-17431.
Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).
Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.
Shriver, Zachary et al., Glycomics: a Pathway to a Class of New and Improved Therapeutics, Nat Rev Drug Disc, 2004, 3, 863-873.
Sieber et al., "Proteomic profiling of metalloprotease activities with cocktails of active-site probes," *Nat. Chem. Biol.*, May 2006, 2(5):274-281.
Sivakumar, Krishnamoorthy et al., "A fluorogenic 1,3-dipolar cycloaddition reaction of 3-azidocoumarins and acetylenes." Org. Lett. 2004,24, 4603-4606.
Skehel, John et al., Receptor Binding and Membrane Fusion in Virus Entry: The Influenza Hemagglutinin, Ann. Rev Biochem, 69:531, 2000.
Sok, Devin et al., SnapShot: Broadly Neutralizing Antibodies. Cell 155, 728-728, (2013).
Solomons, G. and Fryhle, C., Chapter 5 Titled, Stereochemistry: Chiral Molecules, p. 184-228, in "Organic Chemistry," 7th Edition, Wiley, Jun. 18, 2001.
Soriano del Amo, David et al. Chemoenzymatic synthesis of the sialyl Lewis X glycan and its derivatives. Carbohydr. Res. 345, 1107-13, (2010).
Spinosa, Maria Rita et al., The Neisseria Meningitidis Capsule is Important for Intracellular Survival in Huamn Cells, Infect Immun 2001, 75, 3594-3603.
Srinivasan, Quantitative et al., Biochemical Rationale for Differences in Transmissibility of 1918 Pandemic Influenza A Viruses, Proc. Natl. Acad. Sci., 105, 2800-2805, 2008.
Stein, K.E. et al., The Immune Response to an Isomaltohexosyl-Protein Conjugate, a Thymus-Dependent Analogue of Alpha(1 Replaced by 6) Dextran., J Immunol 1982, 128, 1350-1354.
Stein, K.E., Thymus-Independent and Thymus-Dependent Responses to Polysaccharide Antigens, J Infect Dis 1992, 165 Suppl 1, S49-52.
Stephens, David, Conquering the Meningococcus, FEALS Microbial Rev 2007, 31, 3-14.
Stephens, D.S. et al., Epidemic Meningitis, Meningococcaemia, and Neisseria Meningitidis, Lancet 2007, 369, 2196-2210.
Stephenson et al., "Neuraminidase inhibitor resistance after oseltamivir treatment of acute influenza A and B in children," Clin. Infect. Dis., Feb. 15, 2009, 48(4):389-396.
Stevanovic, Stefan, Identification of Tumour-Associated T-Cell Epitopes for Vaccine Development, Nat. Rev. Cancer, 2002, 2, 514-520.
Stevens, James et al., Structure of the Uncleaved Human H1 Hemagglutinin From the Extinct 1918 Influenza Virus, Science, 303:1866, 2004.

(56) References Cited

OTHER PUBLICATIONS

Stevens, James et al., Structure and Receptor Specificity of the Hemagglutinin From an H5N1 Influenza Virus, Science, 312:404, 2006.
Stevens et al., Glycan Microarry Analysis of the Hemagglutinins From Modem and Pandemic Influenza Viruses Reveals Different Receptor Specificities. Journal of Molecular Biology 355.5 (2006): 1143-155.
Stickings, P. et al., nfect. Immun. 2008, 76, 1766.
Stockmann, H. et al., Development and Evaluation of New Cyclootynes for Cell Surface Glycan Imaging in Cancer Cells, J. Chem Sci. 2011, 2, 932-936.
Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.
Stubbs et al., "Synthesis and use of mechanism-based protein-profiling probes for retaining β-D-glucosaminidases facilitate identification of Pseudomonas aeruginosa NagZ," J. Am. Chem. Soc., Jan. 9, 2008, 130(1):327-335.
Su, G. Hahner, W. Zhou "Investigation of the pore formation in anodic aluminum oxide" J Mater. Chem. 2008, 18 5787-5795.
Sun, B., Srinibasan, B., Huang, X., Pre-activation-based one-pot synthesis of an alpha-(2,3)-sialylated core-fucosylated complex type bi-antennary N-glycan dodecasaccharide. Chem Eur. J 14 (23), 7072-81, (2008).
Supplementary European Search Report in European Application No. EP 13775664.9, dated Oct. 27, 2015, in 7 pages.
Sutton, VR et al., Bc1-2 Prevents Apoptosis Induced by Perforin and Granzyme B, But Not That Mediated by Whole Cytotoxic Lymphocytes, J of Immunology 1997, 158(12), 5783.
Tahir et al., "Loss of IFN-γ production by invariant NK T cells in advanced cancer," J. Immunol., Oct. 1, 2001, 167(7):4046-4050.
Takakura, Yoshimitsu et al., Molecular cloning, expression and properties of an alpha/beta-Galactoside alpha 2,3-sialyltransferase from Vibrio sp. JT- FAJ-16. J. Biochem. 142, 403-412, (2007).
Takano, Ryo et al., Sialylation and Malignant Potential in Tumour Cell Glycosylation Mutants, Glycobiology 4, 665-674 (1994).
Taki, Takao et al., Glycolipids of Metastatic Tissue in Liver From Colon Cancer: Appearance of Sialylated Lex and Lex Lipids, J. Biochem. 103, 998-1003, 1998.
Talmadge et al., Murine models to evaluate novel and conventional therapeutic strategies for cancer, Am J. Pathol, 170(3): 793-804 (2007).
Tanaka, Hiroshi et al., An Efficient Convergent Synthesis of GPIc Ganglioside Epitope, J Am Chem Soc. 2008, 130, 17244.
Tanaka, Katsunori et al., Synthesis of a Sialic Acid Containing Complex-Type N-Glycan on a Solid Support, Chemistry—an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.
Thurber, Greg et al., Antibody Tumor Penetration: Transport Opposed by Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.

Toshima, K. Glycosyl fluorides in glycosidations. Carbohydr. Res. 327, 15-26 (2000).
Trinchieri, "Interleukin-12: a proinflammatory cytokine with immunoregulatory functions that bridge innate resistance and antigen-specific adaptive immunity," Annu. Rev. Immunol., 1995, 13:251-276.
Tsai et al., "Design and synthesis of activity probes for glycosidases," Org. Lett., Oct. 17, 2002, 4(21):3607-3610.
Tsai, Charng-sheng et al., Development of Trifunctional Probes for Glycoproteomic Analysis, Chem. Commun. 2010, 46, 5575-5577.
Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., Photobacterium sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Immunol., 13: 437.
Ulrich, G.; Ziessel, R.; Harriman, A. "The chemistry of fluorescent bodipy dyes: Versatility unsurpassed." Angew. Chem. Int. Ed. 2008, 47, 1184-1201.
van der Horst et al., "Photoaffinity labeling of a bacterial sialidase with an aryl azide derivative of sialic acid," J. Biol. Chem., Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Varghese et al., Three-dimensional structure of the complex of 4-guanidino-Neu5Ac2en and nfluenza virus neuraminidase. Protein Sci. Jun. 1995;4(6):1081-7.
Varki, "Glycan-based interactions involving vertebrate sialic-acid-recognizing proteins," Nature, Apr. 26, 2007, 446(7139):1023-1029.
Vasella et al., "Synthesis of a phosphonic acid analogue of N-Acetyl-2,3-didehydro-2-deoxyneuraminic acid, an inhibitor of Vibrio cholerae sialidase," Helv. Chim. Acta., Mar. 13, 1991, 74(2):451-463.
Vavricka, Christopher et al., Influenza Neuraminidase Operates Via a Nucleophilic Mechanism and Can Be Targeted by Covalent Inhibitors, Nature Communcations, 4:1491 (2013).
Vinogradova et al., "Molecular mechanism of lysosomal sialidase deficiency in galactosialidosis involves its rapid degradation," Biochem. J., Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," Angew. Chem. Int. Ed. Engl., Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).

(56) References Cited

OTHER PUBLICATIONS

Wada et al., "A crucial role of plasma membrane-associated sialidase in the survival of human cancer cells," Oncogene, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," Methods Mol. Biol., 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).
Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "*Trypanosoma cruzi* trans-sialidase operates through a covalent sialyl-enzyme intermediate: tyrosine is the catalytic nucleophile," *J. Am. Chem. Soc.*, Jun. 25, 2003, 125(25):7532-7533.
Weibel, Robert et al., Tumor-Associated Membrane Sialoglycoprotein on Human Small Cell Lung Carcinoma Identified by the IgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wilen et al., "Strategies in optical resolutions," Tetrahedron, 1977, 33(21):2725-2736.
Wiltshire, S. et al. Proc. Natl. Acad. Sci. (2000) 97, 10113-10119.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).

Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," Nat. Chem. Biol., Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woo et al. Cytokine profiles induced by the novel swine-origin influenza A/HINI virus: mplications for treatment strategies. J Infect Dis. Feb. 1, 2010;201(3):346-53.
Woyke, Tanja et al., Effect of Auristatin PHE on Microtubule Integrity and Nuclear Localization in Cryptococcus Neoformans, Antimicrob. Agents and Chemother. 45(12): 3580-3584 (2001).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," *Proc. Natl. Acad. Sci. USA*, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Brockman, M. A.; Hodges, B.; Wang, Q. "A fluorogenic 'click' reaction of azidoanthracene derivatives." Tetrahedron 2008, 64, 2906-2914.
Yamaguchi, Kazunori et al., "Evidence for mitochondrial localization of a novel human sialidase (NEU4)," Biochem. J., Aug. 15, 2005, 390(Pt 1):85-93.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yamashita, Yoshito et al., Alterations in Gastric Mucin with Malignant Transformation: Novel Pathway for Mucin Synthesis, (1995) J. Natl. Cancer Inst. 87, 441-446.
Yang, JM et al., Alterations of )-Glycan Biosynthesis in Human Colon Cancer Tissues, (1994) Glycobiology 4, 873-884.
Yaniv, Nature 297: 17-18, 1982.
Yates AJ et al., Brain Tumors in Childhood. Childs Brain 5(1), 31-39 (1979).
Yguembide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Ying et al., One-bead-one-inhibitor-one-substrate screening of neuraminidase activity. Chembiochem. Oct. 2005;6(10):1857-65.
Yoshida M, et al. Glycoconjugate J. 1993, 10, 324.
Yoshimoto et al., "CD4[pos], NK1.1[pos] T cells promptly produce interleukin 4 in response to in vivo challenge with anti-CD3," *J. Exp. Med.*, Apr. 1, 1994, 179(4):1285-1295.
Yuen et al., Human infection by avian influenza A H5N1. Hong Kong Med J. Jun. 2005;1 1(3):189-99.
Zhang et al., "New cerebrosides from Acanthopanax gracilistylus," CAPLUS 156:225776 (2011).
Zheng et al., Delayed antiviral plus immunomodular treatment still reduces mortality in mice infected by high inoculum of influenza A/H5N1 virus. Proc Natl Acad Sci U S A. Jun. 10, 2008;105(23):8091-6.

(56) References Cited

OTHER PUBLICATIONS

Zhou et al., A fluorogenic probe for the copper(I)catalyzed azide-alkyne ligation reaction: modulation of the fluorescence emission via $^3(n,\pi)$-$^1(\pi\pi^*)$ inversion, J. Am. Chem. Soc., Jul. 28, 2004, 126(29):8862-8863.

Zhu, X et al., Mass spectrometric characterization of the glycosylation pattern of HIV-gp120 expressed in CHO cells. Biochemistry 39, 11194-11204 (2000).

Zou, et al., Chemoenzymatic synthesis and Fc gamma receptor binding of homogenous glycoforms of antibody Fc to FcIIIa receptor. J Am Chem Soc. 2011, 133(46):18975-91.

Zimmermann et al., Multi-target therapeutics: when the whole is greater than the sum of the parts. Drug Discov Today. Jan. 2007;12(1-2):34-42. Epub Nov. 28, 2006.

Chu, Kuo-Chinget al., Efficient and Stereoselective Synthesis of [alpha](2->9) Oligosialic Acids: From Monomers to Dodecamers, Angewandte Chemie International Edition, vol. 50, No. 40, Sep. 2011, 9391-9395.

Frank, Natasha et al., The Therapeutic Promise of the Cancer Stem Cell Concept, Journal of Clinical Investigation, 120(1) 41-50, Jan. 2010.

Hsu, Nien-Yeen et al., Desorption Ionization of Biomolecules on Metals, Anal. Chem., 80, 5203-5210, 2008.

Katagiri, Yohko et al Laminin Binding Protein, 34/67 Laminin Receptor, Carries Stage-Specific Embryonic Antigen-4 Epitope Defined By Monoclonal Antibody Raft.2, Biochemical and Biophysical Research Communications, 332, 1004-1011, 2005.

Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.

Merck, MAB4304, Anti-Stage-Specific Embryonic Antigen-4 Antibody, Clone MC-813-70, 4 Pages, 2017.

Moal, E. LE et al., Enhanced Fluorescence Cell Imaging with Metal-Coated Slides, Biophysical Journal, vol. 92, 2150-2161, Mar. 2007.

Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.

Pan, Yanbin et al., Synthesis and Immunological Properties of N-Modified GM3 Antigens as Therapeutic Cancer Vaccines, J. Med. Chem., 48(3), 875-883, 2005.

Shevinsky, LH et al., Monoclonal Antibody to Murine Embryos Defines a Stage-Specific Embryonic Antigen Expressed on Mouse Embryos and Human Teratocarinoma Cells., Cell vol. 30, Issue 3, Oct. 1982, pp. 697-705.

Zhang, Hai-Long et al., A Novel Combined Conjugate Vaccine: Enhanced Immunogenicity of bFGF with CRM197 as a Carrier Protein, Molecular Medicine Reports, 4, 857-863, 2011.

Cheung et al., Meeting Info: 23rd International Symposium on Glycoconjugates, GLYCO 23. Split, Croatia. Sep. 15, 2015-Sep. 20, 2015, vol. 32, No. 5, pp. 323.

International Search Report and Written Opinion in International Application No. PCT/US2017/048074, dated Dec. 26, 2017, 17 pages.

Lei, Jianqing et al., Potential antitumor applications of a monoclonal antibody specifically targeting human papilloma virus 16 E749-57 peptide, Microbiology and Immunology, 2012, vol. 56, pp. 456-462.

Tsai, Charng-Sheng et al., Cell-Permeable Probe for Identification and Imaging of Sialidases, PNAS, vol. 110, No. 7, 2013, 2466-2471.

European Application 14817316.4, Communication pursuant to Article 94(3), dated Apr. 16, 2018, 5 pages.

Greene, Theodora et al., Protective Groups in Organic Synthesis, pp. 42-51 and 96-100, 1991.

Schelhaas, Michael et al., Protecting Group Strategies in Organic Synthesis, Angew. Chem. Int. Ed. Engl. 1996, 35, 2056-2083.

Unverzagt, Carlo et al., A Double Regio- and Stereoselective Glycosylation Strategy for the Synthesis of N-Glycans, Chem. Eur. J., 2008, 14, 1304-1311.

Bacteroides Fragilis NCTC 9343, Complete Genome., Mar. 3, 2005, XP002775523, Database Accession No. CR626927, 2 Pages.

Bacteroides Thetaiotaomicron VPI-5482, Section 8 of 21 of the Complete Genome, XP002775522, Jan. 6, 2006, Database Accession No. AE016933, 2 Pages.

Berg, Jan-Olof et al., Purification of Glycoside Hydrolases From Bacteroides Fragilis, Applied and Environmental Microbiology, vol. 40, No. 1, Jul. 1980, p. 40-47.

Dicker, Martina et al., Using Glyco-Engineering to Produce Therapeutic Proteins, Expert Opinion on Biological Therapy, vol. 15, Jan. 1, 2015, pp. 1501-1516.

Extended European Search Report, App. No. 15799789.1, dated Nov. 28, 2017, 10 Pages.

Extended European Search Report, App. No. 158001917, dated Nov. 28, 2017, 12 Pages.

Extended European Search Report, App. No. 15799981.4, dated Nov. 29, 2017, 9 Pages.

Huang, Wei et al., Chemoenzymatic Glycoengineering of Intact IgG Antibodies for Gain of Functions, Journal American Chemical Socirty, vol. 134, No. 9, Jul. 25, 2012, pp. 12308-12318.

Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.

Lin, Chin-Wei et al., A Common Glycan Structure on Immunoglobulin G for Enhancement of Effector Functions, vol. 112, No. 34, Aug. 7, 2015, pp. 10611-10616.

Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.

Tsai, Tsung-I et al., An Effective Bacterial Ducosidase for Glycoprotein Remodeling, ACS Chemical Biology, vol. 12, No. 1, Jan. 20, 2017, pp. 63-72.

\* cited by examiner

METHODS FOR MODIFYING HUMAN ANTIBODIES BY GLYCAN ENGINEERING

CROSS-REFERENCE TO RELATED APPLICATION(S)

This patent application claims the benefit of U.S. Provisional Patent Application Ser. No. 61/265,757, filed Dec. 2, 2009, entitled "Methods for Modifying Human Antibodies by Glycan Engineering" the content of which is incorporated herein in its entirety by reference.

TECHNICAL FIELD OF THE INVENTION

This invention relates to the field of antibodies. In particular, the application relates to methods for modifying glycosylation states of human monoclonal antibodies (mAbs) by glycan engineering. More particularly, the application relates to uniformly glycosylated glycoforms of Fc regions of human mAbs and methods for preparing the antibodies by glycan engineering.

BACKGROUND OF THE INVENTION

Antibodies, also known as immunoglobulins (Ig), are glycoproteins that play a central role in immune responses. IgG antibodies (Abs) and fragments of IgG Abs have become major biotherapeutics for treating human diseases.

There are five functional classes of immunoglobulins, i.e., immunoglobulin M (IgM), immunoglobulin D (IgD), immunoglobulin G (IgG), immunoglobulin A (IgA) and immunoglobulin E (IgE). Among them, IgG is the most abundant immunoglobulin in serum.

The variable region (Fab) of the antibody molecule is involved in direct binding of the target antigen. All naturally-occurring antibodies each include a constant domain known as the Fc (Fragment, crystallizable) region, which is composed of constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins. By doing this, it mediates different physiological effects including opsonization, cell lysis, and degranulation of mast cells, basophils and eosinophils. (Woof J, Burton D (2004) Nat Rev Immunol 4 (2): 89-99; Heyman B (1996) Immunol. Lett. 54 (2-3): 195-199). Glycosylation of the antibody Fc fragment is essential for Fc receptor-mediated activity. (Peipp M. et al., Blood (2008) 112(6):2390-2399).

The constant (Fc) domain of naturally-occurring antibodies is usually N-glycosylated. The linkage of carbohydrates to proteins occurs through N-linked glycosylation—the attachment of a sugar to the amide nitrogen atom on the side chain of asparagines. The linkage to amino acids is generally embedded in a conserved sequence of amino acids. Glycosylation in the Fc region significantly affects Fc effector functions such as activation of complement (Roos et al., J Immunol. (12):7052-7059.2001) or binding to receptors via their constant (invariable sequence) domains (Mimura et al., J Biol. Chem. 2001 Dec. 7; 276(49):45539-45547; Shields et al., J Biol. Chem. 276(9):6591-6604 (2001)).

It has been found that the sequences of the oligosaccharides attached to Fc regions are essential to the stability and function of the antibodies. For example, the addition of sialic acid (SA), sialylation, at Asn 297 on the Fc domain and terminal galactosylation modify the anti-inflammatory properties of immunoglobulins and play a role in rheumatoid arthritis (RA). (Kaneko, Y et al., Science. (2006) 313(5787): 670-673).

Human antibodies prepared by conventional methods, such as genetic engineering, comprise mixtures of different glycoforms, i.e., containing different oligosaccharides attached to their Fc regions.

The clinical successes of the antibodies rituximab and alemtuzumab for hematological malignancies, and trastuzumab for solid breast tumors, have demonstrated that human or humanized monoclonal antibodies can be useful drugs for the treatment of cancer. All of these antibodies have been approved and are currently in the market. Yet, a need remains for improving this kind of drugs. For instance, rituximab induces a response only in approximately 60% of the patients with relapsed/refractory low-grade non-Hodgkin's lymphoma.

The preferred type of monoclonal antibody for target-cell killing applications is an IgG1-type mAb, where at least the constant (or the Fc) region is of human origin (i.e., chimeric, humanized, or fully-human IgG1s). IgG1 mAbs can exert their therapeutic effects via three classes of mechanisms. Direct binding of the antibody via its variable region to the target molecule on the surface of cancer cells can lead to cell death or inhibition of tumor growth, for example by triggering apoptosis upon cross-linking of target molecules by the antibody. The Fc region operates in the other two-types of mechanisms: complement-mediated cytotoxicity, and Fcγ receptor (FcγR)-dependent effector functions. Some Fc effector functions of IgG1s are mediated by the interactions of the Fc region of target-cell bound antibody molecules and Fcγ receptors on the surface of immune cells. The Fc domains of immunoglobulins have been shown to have effector functions which are primarily complement fixation and Fc receptor (FcR) binding. appropriate glycosylation at the conserved glycosylation site (N297) of the Fc domain is essential for the efficient interactions between mAbs and Fc receptors (FcR) and for the FcR-mediated effector functions, including antibody-dependent cell mediated cytotoxicity (ADCC) and complement-dependent cytotoxicity (CDC). Fc receptors bind to the constant domains of immunoglobulins and a number of receptors have been defined that are thought to mediate accessory functions including opsonization and ADCC (Daeron, M. Annual Review Immunology, (1997) 15; 203-234, Ravetch and Clynes, Annual Review of Immunology. 1998. 16:421-432).

The conserved glycosylation site on the Fc region of antibodies is a target for modulation of antibody effector functions. The crystal structure of a biosynthetic intermediate of human IgG1, bearing immature oligomannose-type glycans and reported to display increased antibody-dependent cellular cytotoxicity, has shown that glycan engineering can bias the Fc to an open conformation primed for receptor binding. (Crispin M., et al., J. Mol. Biol. 387(5):1061-1066 (2009).)

More specifically, certain glycoforms of a human antibody exhibit improved therapeutic effects while others possess undesired properties. For example, de-fucosylated but glycosylated Herceptin® is at least 50-fold more active in the efficacy of Fcγ receptor IIIa mediated ADCC than those with alpha-1,6-linked fucose residues (Shields, R L, et al. J. Biol. Chem., Vol. 277(30):26733-26740, (2002)). Similar results were reported for Rituximab® and other mAbs (Shinkawa T, et al., J. Biol. Chem. (2003) 278:3466-3473).

Strome et al., (WO 2007/146847) disclose a method of preparing antibodies with homogeneous glycosylation states by first deglycosylating an antibody or antibody fragment and then attaching a chemically synthesized sugar to the protein. This method lacks the ability to control the glycosylation process and does not enable control over the conjugation of specific carbohydrates at specific sites during the formation of a desired glycoform. Thus, there is a need for methods of preparing human antibodies comprising desired glycoform(s) wherein the glycosylation is performed in a stepwise manner so as to improve their therapeutic efficacy.

SUMMARY OF THE INVENTION

The invention relates to the Fc region of an antibody molecule, wherein the Fc region is specifically glycosylated with oligosaccharides that increase the efficacy and stability of the Fc region, and the antibody or antibody fragment comprising the Fc region. In some embodiments the specifically glycosylated Fc fragment comprises a monoclonal antibody, preferably a human or humanized monoclonal antibody.

In one aspect, the present invention features an antibody in which both of the Ig domains are attached in the Fc region to oligosaccharides that are free of core fucoses and/or contain terminal sialic acids linked to galactoses. In some embodiments, the oligosaccharides are homogeneous. In some embodiments, the antibody is human or humanized. In some embodiments, the Fc region comprises an antibody or an antibody fragment.

In one embodiment, the terminal sugar units of the invention are sialic acids linked to galactose. N-Acetyl-Neuraminic Acid (Neu5Ac or NANA) is the predominant sialic acid found in mammalian cells. When the human antibody is an IgG, each of its Ig domains can comprise an Fc region containing an N-linked biantenary oligosaccharide with two terminal sialic acids each linked to a galactose, e.g., an oligosaccharide having the structure:

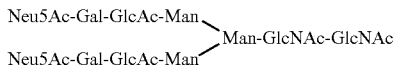

In another aspect, the present invention relates to Fc regions within an antibody or antibody fragment in which both of the Ig domains comprise Fc regions that are attached to either a monosaccharide moiety (e.g., N-Acetylglucosamine, GlcNAc) or a trisaccharide moiety (e.g., Mannose-N-Acetylglucosamine-N-Acetylglucosamine, Man-GlcNAc-GlcNAc).

The invention further relates to methods for preparing the antibodies and antibody fragments disclosed herein.

The invention relates to a method for modifying the Fc region glycosylation pattern of a human or humanized antibody, the method comprising: (a) providing a glycosylated Fc region of a human or humanized antibody; (b) contacting the glycosylated Fc region with alpha-fucosidase under conditions suitable for removing core fucose residues; (c) contacting the de-fucosylated Fc region with β-1,4-galactosyltransferase under conditions suitable for attaching a galactose to the oligosaccharide; and then (d) contacting the Fc region with alpha-2,6-sialyltransferase under conditions suitable for attaching a terminal sialyl residue, thereby producing a modified Fc region of an antibody. When both β-1,4-galactosyltransferase and alpha-2,6-sialyltransferase are used, the antibody to be modified is first contacted with the β-1,4-galactosyltransferase and then the alpha-2,6-sialyltransferase. In some aspects, one or more of alpha-fucosidase, β-1,4-galactosyltransferase and alpha-2,6-sialyltransferase are immobilized on a solid support.

In another aspect, the method comprises: (i) providing a Fc region of an antibody or antibody fragment, wherein the Fc region is glycosylated with an oligosaccharide; (ii) contacting the Fc region with an endo-glycosylase (such as endo-H, endo-F3, etc.) and an exo-glycosylase (such as sialidase, galactosidase, alpha-fucosidase, or a mixture thereof) under conditions wherein the oligosaccharide is digested to a single sugar unit (such as GlcNAc); (iii) elongating the single sugar unit to an oligosaccharide by glycosylation mediated by one or more glycosyltransferases such as endo-N-acetylglucosaminidase, endo-M or endoA; and (iv) contacting the oligosaccharide with alpha-2,6-sialytransferase to add a terminal sialic acid, thereby yielding the antibody having homogeneous oligosaccharides.

In some aspects, the oligosaccharide obtained from the elongating step has a sequence of sugars that is identical to at least a portion of an oligosaccharide comprising a glycosylated Fc region of a naturally-occurring antibody, for example an Ig molecule produced in vivo (either in cell culture or in a host animal). When the antibody is an IgG, the oligosaccharide can have the structure:

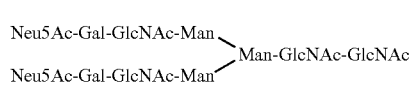 [Structure 1]

The invention further relates to a method for modifying the Fc region glycosylation pattern of a human or humanized antibody, the method comprising: (i) providing a Fc region of an antibody or antibody fragment, wherein the Fc region is glycosylated with an oligosaccharide; (ii) contacting the Fc region with an endo-glycosylase (e.g., endo-H, endo-F3, etc.) and an exo-glycosylase (e.g., sialidase, galactosidase, alpha-fucosidase, or a mixture thereof) under conditions wherein the oligosaccharide is digested to a single sugar unit (e.g., GlcNAc); (iii) elongating the single sugar unit to a first oligosaccharide via glycosylation mediated by glycosyltransferases such as endo-N-acetylglucosaminidase, endo-M or endo-A; (iv) contacting the first oligosaccharide with a β-1,4-galactosyltransferase to produce a second oligosaccharide having a terminal galactose, and (v) contacting the second oligosaccharide with alpha-2,6-sialytransferase to add a terminal sialic acid, thereby yielding an antibody having homogeneous oligosaccharides.

In another embodiment, the method comprises: (i) providing a Fc region of an antibody or antibody fragment, wherein the Fc region is glycosylated with an oligosaccharide; (ii) contacting the Fc region with an exo-glycosylase (e.g., alpha-mannosidase, alpha-fucosidase, sialidase, galactosidase, or a mixture thereof) under conditions wherein the oligosaccharides are trimmed to a trisaccharide (e.g., Man-GlcNAcGlcNAc); (iii) elongating the trisaccharide to an oligosaccharide via glycosylation; and (iv) treating the oligosaccharide with alpha-2,6-sialytransferase to add terminal sialic acids, thereby yielding Fc regions of the antibody population in a single glycoform.

In some embodiments, the Fc region comprises a human IgG sequence and the oligosaccharide has the structure:

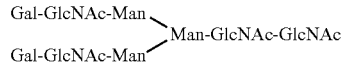

The oligosaccharide is then subjected to alpha-2,6-sialytransferase treatment to add terminal sialic acid residues.

The invention relates to a method for modifying the Fc region glycosylation pattern of a human or humanized antibody, the method comprising: (a) providing a glycosylated Fc region of a human antibody; (b) contacting the glycosylated Fc region with an endo-glycosylase and an exo-glycosylase under conditions wherein the native oligosaccharide is digested to a single sugar unit; (c) contacting the single sugar glycosylated Fc region with a glycosyl transferase under conditions suitable for elongating the single sugar unit to a first oligosaccharide by glycosylation; (d) contacting the first oligosaccharide with β-1,4-galactosyltransferase to produce a second oligosaccharide having a terminal galactoses; and (e) contacting the oligosaccharide with alpha-2,6-sialytransferase under conditions suitable for adding a terminal sialylic acid, thereby producing a modified glycosylated Fc region.

In some embodiments, the Fc region comprises a human IgG sequence and the first oligosaccharide has the structure of:

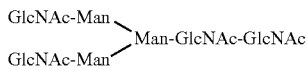

The invention further relates to a method for modifying the Fc region glycosylation pattern of a human or humanized antibody, the method comprising: (a) providing a glycosylated Fc region of a human antibody; (b) contacting the glycosylated Fc region with an endo-glycosylase and an exo-glycosylase under conditions wherein the oligosaccharide is digested to a single sugar unit; (c) contacting the single sugar glycosylated Fc region with a glycosyl transferase under conditions suitable for elongating the single sugar unit to an oligosaccharide by glycosylation; and (d) contacting the oligosaccharide with alpha-2,6-sialytransferase under conditions suitable for adding a terminal sialylic acid, thereby producing a modified glycosylated Fc region.

In some embodiments, the Fc comprises a human IgG and the trisaccharide is ManGlcNAcGlcNAc, wherein the terminal GlcNAc unit of the trisaccharide is attached to the Fc region of the antibody.

In some embodiments, the Fc region comprises a human IgG sequence and the oligosaccharide has the structure:

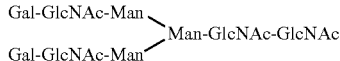

In some embodiments, the elongating step is performed by contacting the trisaccharide sequentially with mannosyltransferase, GlcNAc transferase, and galacosyltransferase.

In some aspects, the endo-glycosidase is selected from the group consisting of: endo-beta-N-acetylglucosaminidases (NAG), endo-H, endo-A and endo-M.

In some aspects, the exo-glycosidase is selected from the group consisting of: s alpha-mannosidase, alpha-fucosidase, sialidase, galactosidase, and a mixture thereof.

In some aspects, the oligosaccharide produced by the elongating step has a sugar sequence identical to an oligosaccharide correlated with efficient FcR-mediated effector functions. In some embodiments thereof, the FcR-mediated effector function is selected from antibody-dependent cell mediated cytotoxicity (ADCC) and complement-dependent cytotoxicity (CDC).

The invention further relates to an antibody or antibody fragment comprising a modified Fc region glycosylation pattern, wherein the Fc region is prepared by any method disclosed herein. In some aspects, the human or humanized antibody is selected from the group consisting of: Reopro®, Rituxan®, Zenepax®, Simulect®, Synagis®, Remicade®, Herceptin®, Mylotarg®, Campath®, Zevalin® Humira®, Xolair®, Bexxar®, Raptiva®, Erbitux®, Avastin®, Tysabri®, a monoclonal antibody, a human or humanized antibody undergoing clinical trials for therapeutic use, and a human or humanized antibody produced by a conventional method.

In some embodiments the invention comprises a plurality of antibody or antibody fragments according to any of the methods disclosed herein, wherein the Fc regions are uniformly glycosylated with the same oligosaccharide sequence.

In another aspect, the invention relates to a human or humanized antibody comprising Fc regions glycosylated at the Fc region with a single glycoform, wherein the antibody is produced by: (a) providing a human or humanized antibody comprising Fc regions glycosylated with heterogeneous glycoforms; and (b) treating the Fc region sequence with a mannosidase and a sialidase under conditions wherein only a trisaccharide is retained at the glycosylation site. In some embodiments, the trisaccharide is ManGlcNAcGlcNAc, and the trisaccharide is conjugated to the Fc region via the terminal GlcNAc residue.

In some aspects, the invention relates to an isolated human antibody, wherein its Fc region is attached to specifically conjugated trisaccharides and are free of other oligosaccharides. In one embodiment, the human antibody is an IgG and at least one of the trisaccharides is ManGlcNAcGlcNAc, in which the terminal GlcNAc unit is attached to the Fc region of the IgG.

In some aspects, the invention relates to a polypeptide comprising the Fc region sequence of an antibody molecule, wherein the polypeptide comprises an N-glycosylation site of the Fc molecule, and further wherein the glycosylation site is conjugated to a monosaccharide, such as GlcNAc. In some aspects, the Fc glycosylation site comprises an asparagine (Asn, N) amino acid residue. In some aspects, the Fc region comprises an IgG antibody and the N-glycosylation site is Asn-297 residue. In some embodiments, the polypeptide comprises an antibody, or a human or humanized antibody. In some embodiments, the human or humanized antibody comprises Fc regions glycosylated with a single glycoform comprising the monosaccharide, GlcNAc.

In some aspects, the polypeptide comprises an N-glycosylation site of the Fc molecule, and further wherein the glycosylation site is conjugated to a trisaccharide. In some embodiments, the trisaccharide is ManGlcNAcGlcNAc, and the trisaccharide is conjugated to the Fc region via the terminal GlcNAc residue.

In some aspects, the invention relates to a human or humanized antibody comprising Fc regions glycosylated at the Fc region with a single glycoform, wherein the antibody is produced by: (a) providing a human or humanized antibody comprising Fc regions glycosylated with heterogeneous glycoforms; and (b) treating the Fc region sequence with a galactosidase and a sialidase under conditions wherein only a monosaccharide is retained at the glycosylation site. In some embodiments, the monosaccharide is GlcNAc. In some embodiments, the human or humanized antibody comprises Fc regions glycosylated with a single glycoform comprising the trisaccharide, ManGlcNAcGlcNAc.

The details of one or more embodiments of the invention are set forth in the description below. Other features or advantages of the present invention will be apparent from the following drawing and detailed description of several embodiments, and also from the appended claims.

DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
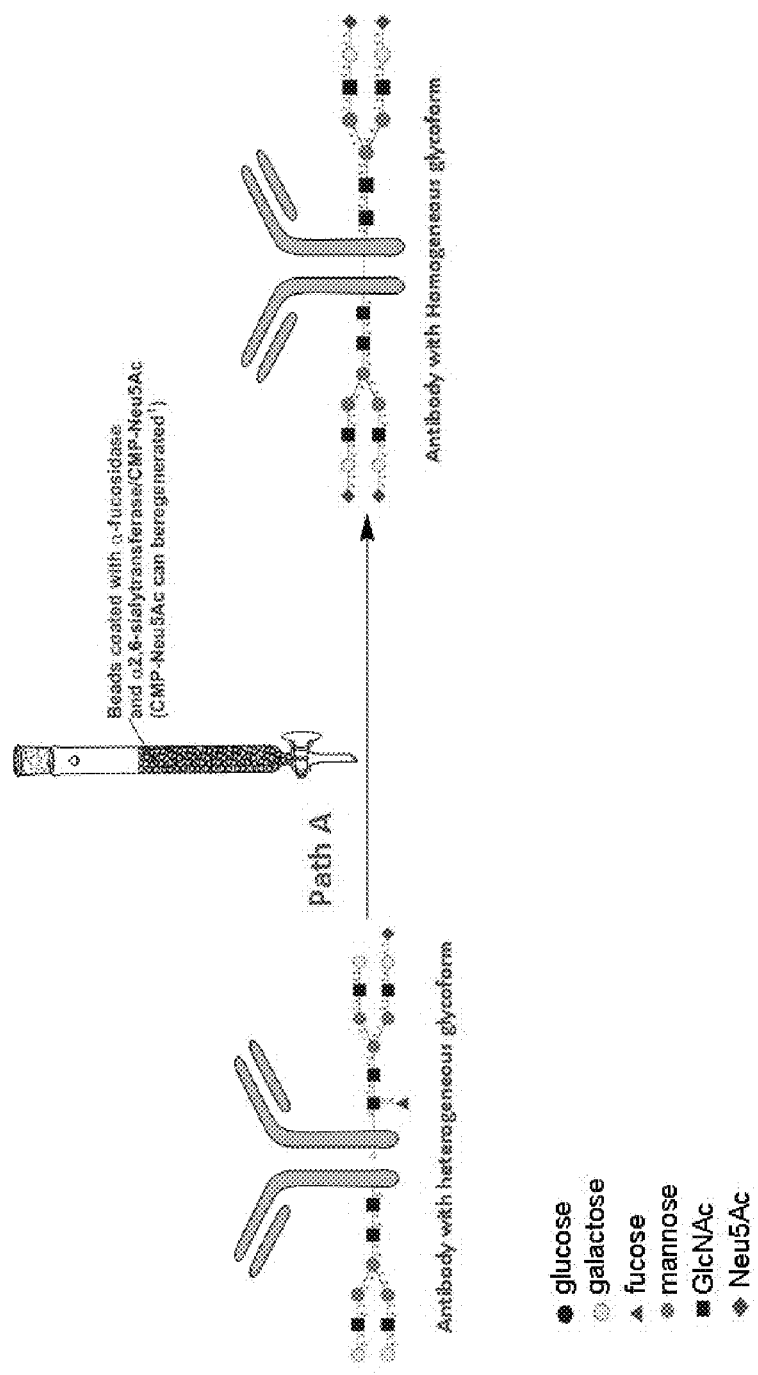
FIG. 1 shows a schematic illustration depicting a pathway (Path A) for modifying a human antibodies by glycan engineering, using alpha-fucosidase, alpha-2,6-sialyltransferase, and optionally β-1,4-galactosyltransferase.

Disclosed herein are modified human antibodies prepared via glycan engineering. The invention relates to the Fc region of an antibody molecule, wherein the Fc region is specifically glycosylated with oligosaccharides that increase the efficacy and stability of the Fc region, and the antibody or antibody fragment comprising the Fc region. In some embodiments the specifically glycosylated Fc fragment comprises a monoclonal antibody, preferably a human or humanized monoclonal antibody. Methods for generating such Fc glycosylated antibodies or antibody fragments by glycan engineering are disclosed herein In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

Definitions

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press, 1989); DNA Cloning, Volumes I and II (D. N. Glover ed., 1985); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds), Immunochemical Methods In Cell And Molecular Biology (Mayer and Walker, eds., Academic Press, London, 1987); Antibodies: A Laboratory Manual, by Harlow and Lane s (Cold Spring Harbor Laboratory Press, 1988); and Handbook Of Experimental Immunology, Volumes I-IV (D. M. Weir and C. C. Blackwell, eds., 1986).

As used herein, the term "glycan" refers to a polysaccharide, or oligosaccharide. Glycan is also used herein to refer to the carbohydrate portion of a glycoconjugate, such as a glycoprotein, glycolipid, glycopeptide, glycoproteome, peptidoglycan, lipopolysaccharide or a proteoglycan. Glycans usually consist solely of β-glycosidic linkages between monosaccharides. For example, cellulose is a glycan (or more specifically a glucan) composed of β-1,4-linked D-glucose, and chitin is a glycan composed of β-1,4-linked N-acetyl-D-glucosamine. Glycans can be homo or heteropolymers of monosaccharide residues, and can be linear or branched. Glycans can be found attached to proteins as in glycoproteins and proteoglycans. They are generally found on the exterior surface of cells. O- and N-linked glycans are very common in eukaryotes but may also be found, although less commonly, in prokaryotes. N-Linked glycans are found attached to the R-group nitrogen (N) of asparagine in the sequon. The sequon is a Asn-X-Ser or Asn-X-Thr sequence, where X is any amino acid except praline.

The term "exo-glycosylase" used herein refers to an enzyme capable of hydrolysis of glycan structure from the out most non-reducing end. Examples of suitable exo-glycosylase include, but are not limited to sialidase, galactosidase, alpha-fucosidase, alpha-mannosidase. The term "endo-glycosylase" used herein refers to an enzyme capable of hydrolysis of glycan structures randomly from the inner sits of whole glycan. Examples include, but are not limited to Endo-H, Endo-F3, Endo-F2, and Endo-F1.

The term "antibody" (Ab) as used herein includes monoclonal antibodies, polyclonal antibodies, multispecific antibodies (e.g., bispecific antibodies), and antibody fragments, so long as they exhibit the desired biological activity. The term "immunoglobulin" (Ig) is used interchangeably with "antibody" herein.

The term "isolated antibody" used herein refers to an antibody substantially free from naturally associated molecules, i.e., the naturally associated molecules constituting at most 20% by dry weight of a preparation containing the antibody. Contaminant components of its natural environment are materials that would interfere with diagnostic or therapeutic uses for the antibody, and may include enzymes, hormones, and other proteinaceous or nonproteinaceous solutes. In preferred embodiments, the antibody is purified: (1) to greater than 95% by weight of antibody as determined by the Lowry method, and most preferably more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie Blue or, preferably, silver stain. Isolated antibody includes the antibody in situ within recombinant cells since at least one component of the antibody's natural environment will not be present. Ordinarily, however, isolated antibody will be prepared by at least one purification step. Purity can be measured by any appropriate method, e.g., column chromatography, polyacrylamide gel electrophoresis, and HPLC.

A "human antibody" as used herein refers to an antibody naturally existing in humans, a functional fragment thereof, or a humanized antibody, i.e., a genetically engineered antibody a portion of which (e.g., a frame region or the Fc region) derives from a naturally-occurring human antibody.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222: 581-597 (1991), for example.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β,β-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56(L2) and 89-97 (L3) in the VL, and around about 31-35 (H1), 50-65 (H2) and 95-102 (H3) in the VH when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the VL, and 26-32 (H1), 52-56 (H2) and 95-101 (H3) in the VH when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the VL, and 27-38 (H1), 56-65 (H2) and 105-120 (H3) in the VH when numbered in accordance with the IMGT numbering system; Lefranc, M.P. et al. Nucl. Acids Res. 27:209-212 (1999), Ruiz, M. e al. Nucl. Acids Res. 28:219-221 (2000)). Optionally the antibody has symmetrical insertions at one or more of the following points 28, 36 (L1), 63, 74-75 (L2) and 123 (L3) in the VL, and 28, 36 (H1), 63, 74-75 (H2) and 123 (H3) in the VH when numbered in accordance with Honegger, A. and Plukthun, A. J. Mol. Biol. 309:657-670 (2001)).

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., Proc. Natl. Acad. Sci. USA, 81:6851-6855 (1984)). The present invention provides variable domain antigen-binding sequences derived from human antibodies. Accordingly, chimeric antibodies of primary interest herein include antibodies having one or more human antigen binding sequences (e.g., CDRs) and containing one or more sequences derived from a non-human antibody, e.g., an FR or C region sequence. In addition, chimeric antibodies of primary interest herein include those comprising a human variable domain antigen binding sequence of one antibody class or subclass and another sequence, e.g., FR or C region sequence, derived from another antibody class or subclass. Chimeric antibodies of interest herein also include those containing variable domain antigen-binding sequences related to those described herein or derived from a different species, such as a non-human primate (e.g., Old World Monkey, Ape, etc). Chimeric antibodies also include primatized and humanized antibodies.

Furthermore, chimeric antibodies may comprise residues that are not found in the recipient antibody or in the donor antibody. These modifications are made to further refine antibody performance. For further details, see Jones et al., Nature 321:522-525 (1986); Riechmann et al., Nature 332: 323-329 (1988); and Presta, Curr. Opin. Struct. Biol. 2:593-596 (1992).

A "humanized antibody" is generally considered to be a human antibody that has one or more amino acid residues introduced into it from a source that is non-human. These non-human amino acid residues are often referred to as "import" residues, which are typically taken from an "import" variable domain. Humanization is traditionally performed following the method of Winter and co-workers (Jones et al., Nature, 321:522-525 (1986); Reichmann et al., Nature, 332:323-329 (1988); Verhoeyen et al., Science, 239:1534-1536 (1988)), by substituting import hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species.

A "human antibody" is an antibody containing only sequences present in an antibody naturally produced by a human. However, as used herein, human antibodies may comprise residues or modifications not found in a naturally occurring human antibody, including those modifications and variant sequences described herein. These are typically made to further refine or enhance antibody performance.

An "intact" antibody is one that comprises an antigen-binding site as well as a CL and at least heavy chain constant domains, CH 1, CH 2 and CH 3. The constant domains may be native sequence constant domains (e.g., human native sequence constant domains) or amino acid sequence variant thereof. Preferably, the intact antibody has one or more effector functions.

An "antibody fragment" comprises a portion of an intact antibody, preferably the antigen binding or variable region of the intact antibody. Examples of antibody fragments include Fab, Fab', F(ab')2, and Fv fragments; diabodies; linear antibodies (see U.S. Pat. No. 5,641,870; Zapata et al., Protein Eng. 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH 1). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

An antibody having a "biological characteristic" of a designated antibody is one that possesses one or more of the biological characteristics of that antibody which distinguish it from other antibodies. For example, in certain embodiments, an antibody with a biological characteristic of a designated antibody will bind the same epitope as that bound by the designated antibody and/or have a common effector function as the designated antibody.

An "antibody that inhibits the growth of infected cells" or a "growth inhibitory" antibody is one that binds to and results in measurable growth inhibition of infected cells expressing or capable of expressing an HIV1 epitope bound by an antibody. Preferred growth inhibitory antibodies inhibit growth of infected cells by greater than 20%, preferably from about 20% to about 50%, and even more preferably, by greater than 50% (e.g., from about 50% to about 100%) as compared to the appropriate control, the control typically being infected cells not treated with the antibody being tested. Growth inhibition can be measured at an antibody concentration of about 0.1 to 30 µg/ml, or about 0.5 nM to 200 nM in cell culture, where the growth inhibition is determined 1-10 days after exposure of the infected cells to the antibody. Growth inhibition of infected cells in vivo can be determined in various ways known in the art. The antibody is growth inhibitory in vivo if administration of the antibody at about 1 mg/kg to about 100 mg/kg body weight results in reduction the percent of infected cells or total number of infected cells within about 5 days to 3 months from the first administration of the antibody, preferably within about 5 to 30 days.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or U.S. Pat. No. 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., Proc. Natl. Acad. Sci. (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (reviewed by M. Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., Eur. J. Immunol. 24:2429-2434 (1994)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1997), may be performed.

A "mammal" for purposes of treating an infection, refers to any mammal, including humans, domestic and farm animals, and zoo, sports, or pet animals, such as dogs, cats, cattle, horses, sheep, pigs, goats, rabbits, etc. Preferably, the mammal is human.

"Treating" or "treatment" or "alleviation" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject or mammal is successfully "treated" for an infection if, after receiving a therapeutic amount of an antibody according to the methods of the present invention, the patient shows observable and/or measurable reduction in or absence of one or more of the following: reduction in the number of infected cells or absence of the infected cells; reduction in the percent of total cells that are infected; and/or relief to some extent, one or more of the symptoms associated with the specific infection; reduced morbidity and mortality, and improvement in quality of life issues. The above parameters for assessing successful treatment and improvement in the disease are readily measurable by routine procedures familiar to a physician.

The term "therapeutically effective amount" refers to an amount of an antibody or a drug effective to "treat" a disease or disorder in a subject or mammal See preceding definition of "treating."

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

Administration "in combination with" one or more further therapeutic agents includes simultaneous (concurrent) and consecutive administration in any order.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ polyethylene glycol (PEG), and PLURONICS™

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below.

A "growth inhibitory agent" when used herein refers to a compound or composition which inhibits growth of a cell, either in vitro or in vivo. Examples of growth inhibitory agents include agents that block cell cycle progression, such as agents that induce G1 arrest and M-phase arrest. Classic M-phase blockers include the vinca alkaloids (vincristine, vinorelbine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (W B Saunders: Philadelphia, 1995), especially p. 13. The taxanes (paclitaxel and docetaxel) are anticancer drugs both derived from the yew tree. Docetaxel (TAXOTERE™, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

The term "polypeptide" is used in its conventional meaning, i.e., as a sequence of amino acids. The polypeptides are not limited to a specific length of the product. Peptides, oligopeptides, and proteins are included within the definition of polypeptide, and such terms may be used interchangeably herein unless specifically indicated otherwise. This term also does not refer to or exclude post-expression modifications of the polypeptide, for example, glycosylations, acetylations, phosphorylations and the like, as well as other modifications known in the art, both naturally occurring and non-naturally occurring. A polypeptide may be an entire protein, or a subsequence thereof. Particular polypeptides of interest in the context of this invention are amino acid subsequences comprising CDRs and being capable of binding an antigen or HIV-infected cell.

An "isolated polypeptide" is one that has been identified and separated and/or recovered from a component of its natural environment. In preferred embodiments, the isolated polypeptide will be purified (1) to greater than 95% by weight of polypeptide as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or non-reducing conditions using Coomassie blue or, preferably, silver stain. Isolated polypeptide includes the polypeptide in situ within recombinant cells since at least one component of the polypeptide's natural environment will not be present. Ordinarily, however, isolated polypeptide will be prepared by at least one purification step.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

Antibodies of the Invention

The antibodies and antibody fragments of the invention are glycosylated in their Fc regions with oligosaccharides that are (a) free of core fucoses and/or (b) include terminal sialic acids linked to galactoses. Preferably, the oligosaccharides are homogeneous. In some aspects the antibodies are human or humanized. Where the Fc receptor binding protein is derived from the human IgG1 immunoglobulin or the human IgG3 immunoglobulin, the sequence of the Cγ2 domain present within the Fc receptor binding protein retains a highly-conserved N-linked glycosylation site at the asparagine (Asn, N) residue at position 297 (N297). The glycosylation of this residue has been identified as being important for mediating high affinity binding and activation of Fc receptors.

In one embodiment, the terminal sugar units of the invention are sialic acids linked to galactose. When the modified human or humanized antibodies are IgG molecules, the oligosaccharide moieties attached to the Fc regions can have the structures:

[Structure I]

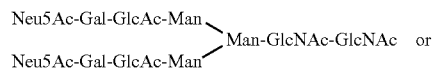

or

[Structure II]

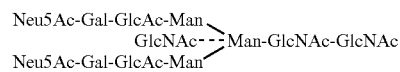

Disclosed herein is an antibody or antibody fragment in which both Ig domains comprise Fc regions that are attached to a monosaccharide moiety (e.g., N-Acetylglucosamine, GlcNAc) or a trisaccharide moiety (e.g., Mannose-N-Acetylglucosamine-N-Acetylglucosamine, Man-GlcNAc-GlcNAc).

Preferably, the trisaccharides are identical to the trisaccharide portions of the oligosaccharides attached to Fc regions of naturally-occurring human antibodies. When the antibodies are IgG molecules, the trisaccharides can have the structure of Man-GlcNAc-GlcNAc.

Any of the antibodies of this invention can be prepared from a commercially available therapeutic antibody (e.g., Reopro®, Rituxan®, Zenepax®, Simulect®, Synagis®, Remicade®, Herceptin®, Mylotarg®, Campath®, Zevalin®, Humira®, Xolair®, Bexxar®, Raptiva®, Erbitux®, Avastin®, Tysabri®), human or humanized antibodies produced via a conventional method, preferably those undergoing clinical trials.

Other monoclonal antibodies suitable for this invention include, but are not limited to Cetuximab®, Rituximab®, Muromonab-CD3®, Abciximab®, Daclizumab®, Basiliximab®, Palivizumab®, Infliximab®, Trastuzumab®, Gemtuzumab Ozogamicin®, Alemtuzumab®, Ibritumomab Tiuxetan®, Adalimumab®, Omalizumab®, Tositumomab®, 1-131 Tositumomab®, Efalizumab®, Bevacizumab®, Panitumumab®, Pertuzumab®, Natalizumab®, Etanercept®, IGN101®, Volociximab®, Anti-CD80 Mab, Anti-CD23 Mab, CAT-3888®, CDP-791®, Eraptuzumab®, MDX-010®, MDX-060®, MDX-070®, Matuzumab® CP-675®, 206®, CAL®, SGN-30® Zanolimumab® Adecatumumab®, Oregovomab®, Nimotuzumab®, ABT-874®, Denosumab®, AM 108®, AMG 714®, Fontolizumab, Daclizumab®, Golimuma®, CNTO 1275®, Ocrelizumab®, Humax-CD20®, Belimumab®, Epratuzumab®, MLN1202®, Visilizumab®, Tocilizumab®, Ocrerlizumab®, Certolizumab Pegol®, Eaulizumab®, Pexelizumab®, Abciximab®, Ranibizimumab®, Mepolizumab®, TNX-355®, and MYO-029®.

The antibodies of the present invention may be polyclonal or monoclonal antibodies. However, in preferred embodiments, they are monoclonal. In particular embodiments, antibodies of the present invention are human antibodies. Methods of producing polyclonal and monoclonal antibodies are known in the art and described generally, e.g., in U.S. Pat. No. 6,824,780. Typically, the antibodies of the present invention are produced by recombinant techniques, using vectors and methods available in the art, as described further below. Human antibodies may also be generated by in vitro activated B cells (see U.S. Pat. Nos. 5,567,610 and 5,229,275).

Human antibodies may also be produced in transgenic animals (e.g., mice) that are capable of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice results in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggemann et al., Year in Immunology, 7:33 (1993); U.S. Pat. Nos. 5,545,806, 5,569,825, 5,591,669 (all of GenPharm); U.S. Pat. No. 5,545,807; and WO 97/17852. Such animals may be genetically engineered to produce human antibodies comprising a polypeptide of the present invention.

In certain embodiments, antibodies of the present invention are chimeric antibodies that comprise sequences derived from both human and non-human sources. In particular embodiments, these chimeric antibodies are humanized or Primatized™ In practice, humanized antibodies are typically human antibodies in which some hypervariable region residues and possibly some FR residues are substituted by residues from analogous sites in rodent antibodies.

The choice of non-human sequences, both light and heavy, to be used in making the chimeric antibodies is important to reduce antigenicity and human anti-non-human antibody responses when the antibody is intended for human therapeutic use. It is further important that chimeric antibodies retain high binding affinity for the antigen and other favorable biological properties. To achieve this goal, according to a preferred method, chimeric antibodies are prepared by a process of analysis of the parental sequences and various conceptual chimeric products using three-dimensional models of the parental human and non-human sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

As noted above, antibodies (or immunoglobulins) can be divided into five different classes, based on differences in the amino acid sequences in the constant region of the heavy chains. All immunoglobulins within a given class have very similar heavy chain constant regions. These differences can be detected by sequence studies or more commonly by serological means (i.e. by the use of antibodies directed to these differences). Antibodies, or fragments thereof, of the present invention may be any class, and may, therefore, have a gamma, mu, alpha, delta, or epsilon heavy chain. A gamma chain may be gamma 1, gamma 2, gamma 3, or gamma 4; and an alpha chain may be alpha 1 or alpha 2.

In a preferred embodiment, an antibody of the present invention, or fragment thereof, is an IgG. IgG is considered the most versatile immunoglobulin, because it is capable of carrying out all of the functions of immunoglobulin molecules. IgG is the major Ig in serum, and the only class of Ig that crosses the placenta. IgG also fixes complement, although the IgG4 subclass does not. Macrophages, monocytes, PMN's and some lymphocytes have Fc receptors for the Fc region of IgG. Not all subclasses bind equally well; for example, IgG2 and IgG4 do not bind to Fc receptors. A consequence of binding to the Fc receptors on PMN's, monocytes and macrophages is that the cell can now internalize the antigen better. IgG is an opsonin that enhances phagocytosis. Binding of IgG to Fc receptors on other types of cells results in the activation of other functions. Antibodies of the present invention may be of any IgG subclass.

In another preferred embodiment, an antibody, or fragment thereof, of the present invention is an IgE. IgE is the least common serum Ig since it binds very tightly to Fc receptors on basophils and mast cells even before interacting with antigen. As a consequence of its binding to basophils and mast cells, IgE is involved in allergic reactions. Binding of the allergen to the IgE on the cells results in the release of various pharmacological mediators that result in allergic symptoms. IgE also plays a role in parasitic helminth diseases. Eosinophils have Fc receptors for IgE and binding of eosinophils to IgE-coated helminths results in killing of the parasite. IgE does not fix complement.

As noted above, the present invention further provides antibody fragments comprising a polypeptide of the present invention. In certain circumstances there are advantages of using antibody fragments, rather than whole antibodies. For example, the smaller size of the fragments allows for rapid clearance, and may lead to improved access to certain tissues, such as solid tumors. Examples of antibody fragments include: Fab, Fab', F(ab')$_2$ and Fv fragments; diabodies; linear antibodies; single-chain antibodies; and multispecific antibodies formed from antibody fragments.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells.

In certain embodiments, antibodies of the present invention are bispecific or multi-specific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-HIV1 arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and FcγRIII (CD16), so as to focus and localize cellular defense mechanisms to the infected cell. Bispecific antibodies may also be used to localize cytotoxic agents to infected cells. These antibodies possess an HIV1-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies). WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

Antibodies with more than two valencies are contemplated. For example, trispecific antibodies can be prepared. Tutt et al., J. Immunol. 147: 60 (1991). A multivalent antibody may be internalized (and/or catabolized) faster than a bivalent antibody by a cell expressing an antigen to which the antibodies bind. The antibodies of the present invention can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$—Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a $C_L$ domain. Antibodies of the present invention further include single chain antibodies.

Methods for preparing any of the human antibodies described above are disclosed.

In one example, this method includes (i) providing a human antibody, which is glycosylated in the Fc region; and (ii) contacting the antibody with alpha-fucosidase, alpha-2,6-sialyltransferase, and optionally β-1,4-galactosyltransferase to modify the oligosaccharides contained in the antibody, thereby producing a human antibody of this invention. When both β-1,4-galactosyltransferase and alpha-2,6-sialyltransferase are used, the antibody to be modified must first contact with the β-1,4-galactosyltransferase and then the alpha-2,6-sialyltransferase. Alpha-2,6-sialyltransferase and β-galactosyltransferase transfer a sialic acid and a galactose, respectively, to an oligosaccharide via a glycosidic bond. In one example, the alpha-fucosidase and one of the β-1,4-galactosyltransferase and alpha-2,6-sialyltransferase can be immobilized on a support member (e.g., a bead). FIG. 1 shows a schematic illustration depicting the pathway (Path A)

Figure 2:
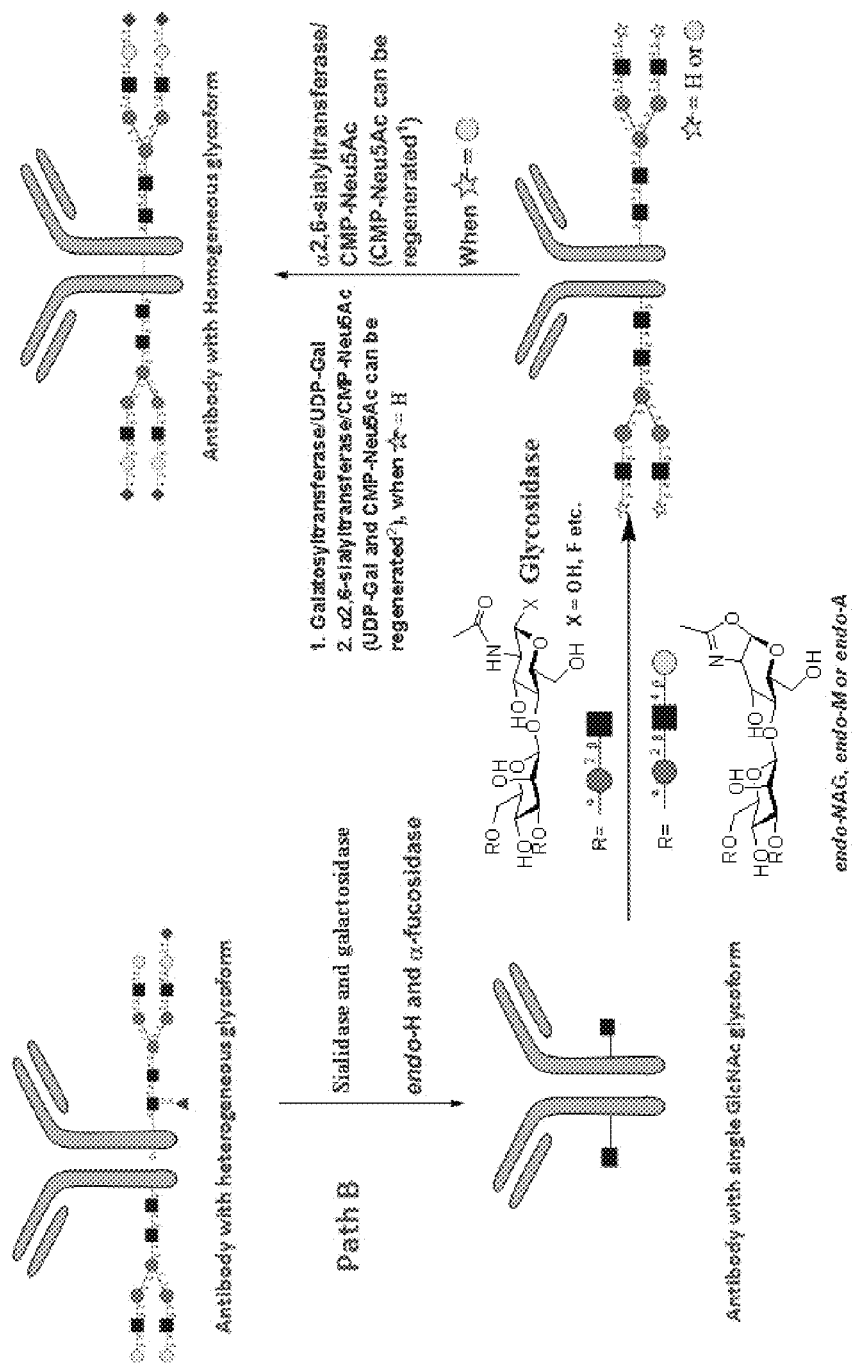
FIG. 2 shows a schematic illustration depicting a chemoenzymatic pathway (Path B) for preparing human antibodies in a single glycoform by glycan engineering, using various exo-glycosidases, endo-glycosidases, and glycosyltransferases.

FIG. 2 shows a schematic illustration depicting a chemoenzymatic pathway (Path B) for preparing human antibodies with a single glycoform by glycan engineering, using various exo-glycosidases, endo-glycosidases, and glycosyltransferases. The method the method comprises: (i) providing a Fc region of an antibody or antibody fragment, wherein the Fc region is glycosylated with an oligosaccharide; (ii) contacting the Fc region with an endo-glycosylase (such as endo-H, endo-F3, etc.) and an exo-glycosylase (such as sialidase, galactosidase, alpha-fucosidase, or a mixture thereof) under conditions wherein the oligosaccharide is digested to a single sugar unit (such as GlcNAc); (iii) elongating the single sugar unit to an oligosaccharide by glycosylation mediated by one or more glycosyltransferases such as endo-N-acetylglucosaminidase, endo-M or endo-A; and (iv) contacting the oligosaccharide with alpha-2,6-sialyltransferase to add a terminal sialic acid, thereby yielding the antibody having homogeneous oligosaccharides.

The oligosaccharide obtained from the elongating step can have a sugar sequence identical to at least a portion of an oligosaccharide found in a naturally-occurring antibody, i.e., a whole Ig molecule produced in a cell (either in cell culture or in a host animal) that glycosylates the Ig molecule in its Fc region. When the antibody is an IgG, the oligosaccharide can have the structure of:

[Structure I]

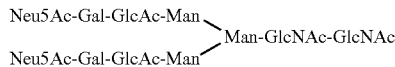

In yet another example, the method of this invention comprises five steps: (i) providing a Fc region of an antibody or antibody fragment, wherein the Fc region is glycosylated with an oligosaccharide; (ii) contacting the Fc region with an endo-glycosylase (e.g., endo-H, endo-F3, etc.) and an exo-glycosylase (e.g., sialidase, galactosidase, alpha-fucosidase, or a mixture thereof) under conditions wherein the oligosaccharide is digested to a single sugar unit (e.g., GlcNAc); (iii) elongating the single sugar unit to a first oligosaccharide via glycosylation mediated by glycosyltransferases such as endo-N-acetylglucosaminidase, endo-M or endo-A; (iv) contacting the first oligosaccharide with a β-1,4-galactosyltransferase to produce a second oligosaccharide having a terminal galactose, and (v) contacting the second oligosaccharide with alpha-2,6-sialyltransferase to add a terminal sialic acid, thereby yielding antibody populations having Fc regions glycosylated with homogeneous oligosaccharides.

Figure 3:
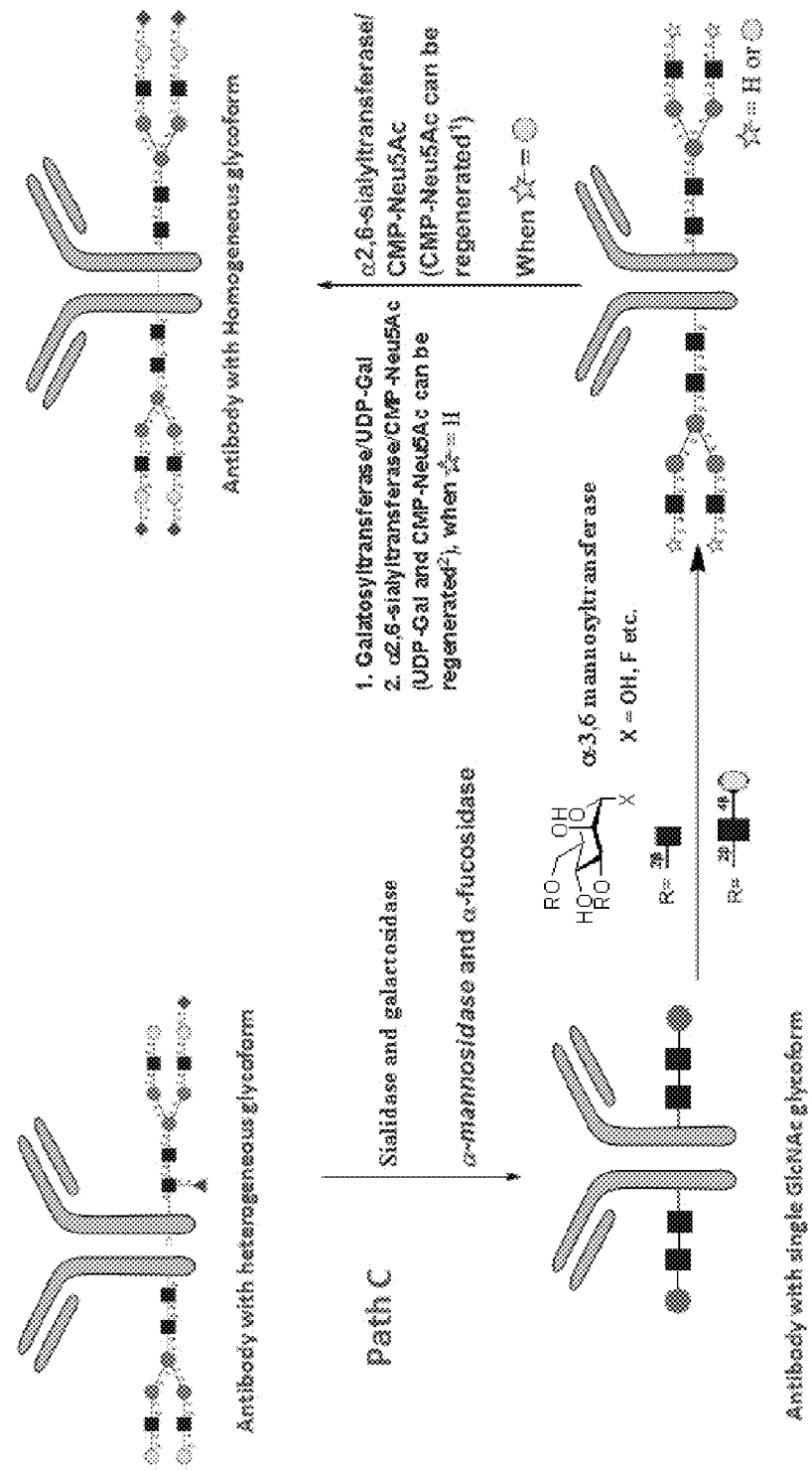
FIG. 3 shows a schematic illustration depicting an enzymatic pathway (Path C) for preparing human antibodies in a single glycoform by glycan engineering, using various exo-glycosidases and glycosyltransferases.
Figure 4:
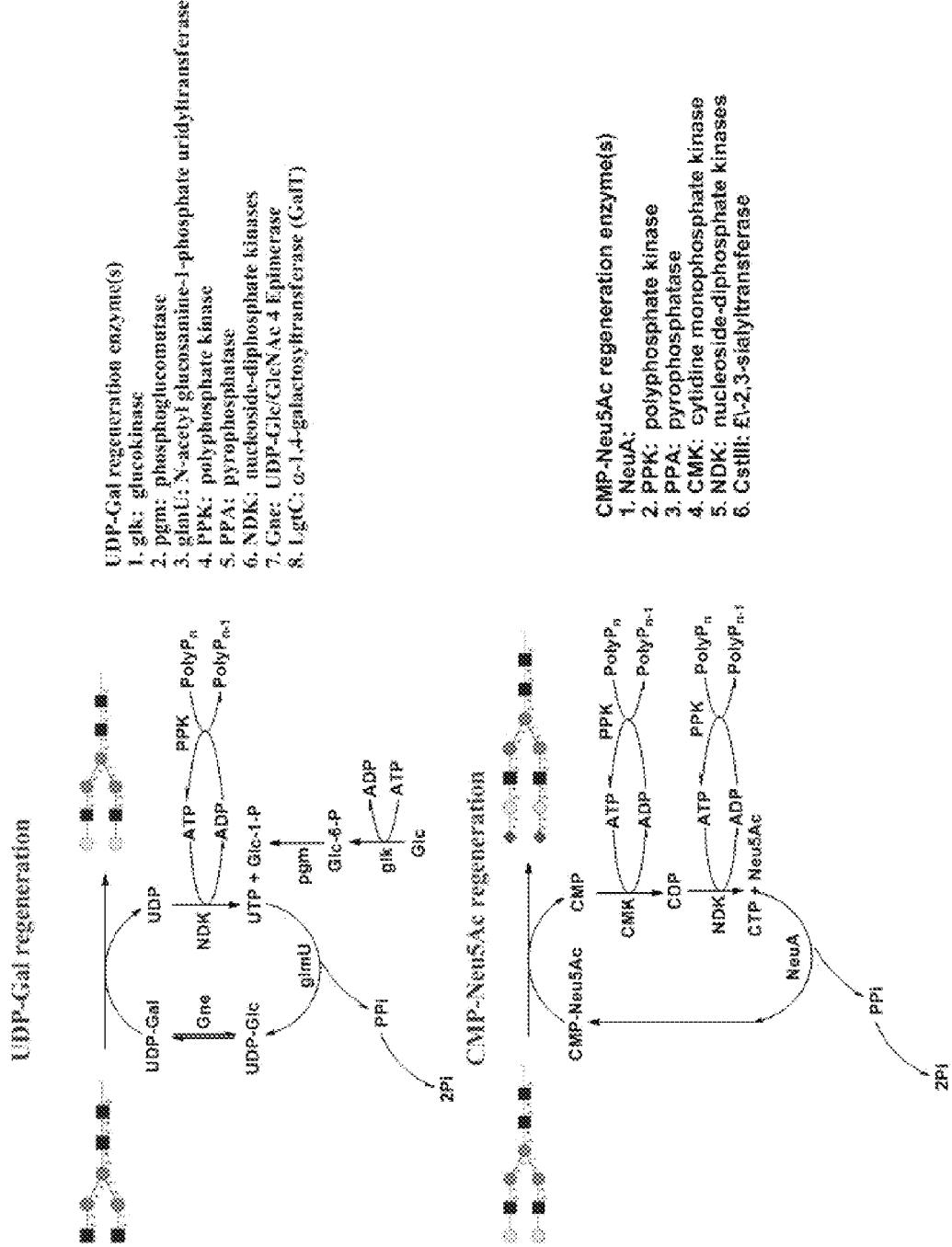
FIG. 4 shows a schematic illustration depicting the regeneration of the cofactor CMP-Neu5Ac and UDP-galactose.

In still another example, the method of this invention is performed as follows: (i) providing a human antibody, the Fc region of which is attached to oligosaccharides; (ii) treating the antibody with an exo-glycosylase (e.g., alpha-mannosidase, alpha-fucosidase, sialidase, galactosidase, or a mixture thereof) to trim each of the oligosaccharides to a trisaccharide (e.g., ManGlcNAcGlcNAc); (iii) elongating the trisaccharide to an oligosaccharide via glycosylation; and (iv) treating the oligosaccharide with alpha-2,6-sialyltransferase to add terminal sialic acids, thereby yielding the antibody in a single glycoform. FIG. 3 shows a schematic illustration depicting such an enzymatic pathway (Path C).

Preferably, the oligosaccharide obtained from the elongating step has a sugar sequence identical to a portion of an oligosaccharide found in the Fc region of a naturally occurring human antibody. When the antibody is an IgG, the oligosaccharide can have the structure of:

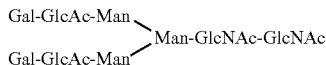

The oligosaccharide is then subjected to alpha-2,6-sialyltransferase treatment to add terminal sialic acid residues.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Method A for Making Antibodies of the Invention

Following Path A depicted in FIG. 1, a human antibody can be treated with α-fucosidase to remove core fucoses and with α-2,6-siayltransferase to add terminal α-2,6-linked sialic acids. When necessary, it can be treated with β-1,4-galactosyltransferase to add a galactose and then with α-2,6-siayltransferase to add the terminal α-2,6-linked sialic acids. Preferably, the enzymes used in this method can be immobilized on a support member. In one example, α-fucosidase and α-2,6-siayltransferase are coated onto a plurality of beads and the resultant coated beads are packed in a column. A sample containing an antibody, either obtained from a commercial vendor or produced by a conventional method, is then loaded onto the column under conditions suitable for the enzymatic reactions catalyzed by the α-fucosidase and α-2,6-siayltransferase. The antibody, with core fucose removed and terminal sialic acid added, is then eluted by a suitable solution.

Example 2

Method B for Making Antibodies of the Invention

Alternatively, an antibody of this invention can be prepared following Path B described in FIG. 2. FIG. 2 shows an example for preparing an IgG antibody with its Fc region glycosylated with biantennary N-linked oligosaccharides. A human IgG antibody, having a glycosylated Fc region, was treated with sialidase and galactosidase, followed by Endo-H and alpha-fucosidase to produce an antibody having both Ig domains in the Fc region attached to a single GlcNAc residue. The antibody having two single GlcNAc residues attached (one in each of the Ig domains) is then subjected to endoglycosidase-catalyzed transglycosylation to elongate each of the GlcNAc residues to an oligosaccharide. In one example, a synthetic oligosaccharide with suitable leaving group like —OH, F or others is added to the GlcNAc mono-saccharide on the modified antibody via a glycosidase enzyme. Another example is a synthetic oligosaccharide with oxazoline group is added to the GlcNAc residue via an endo-beta-N-acetylglucosaminidase (NAG), endo-A or endo-M-mediated enzymatic reaction. The oligosaccharide is then treated with α-2,6-siayltransferase in the presence of CMP-Neu5Ac to add a terminal sialic acid residues. When necessary, a galactose residue is added to the oligosaccharide via β-1,4-galactosyltransferase, using UDP-Gal as a substrate, before addition of the sialic acids.

Example 3

Method C for Making Antibodies of the Invention

An antibody of this invention can also be prepared following the process (i.e., Path C) depicted in FIG. 3. In this process, a human antibody with glycosylated Fc region can be first treated with one or more exo-glycosylases to remove core fucoses and to trim the original oligosaccharides attached to the Fc region to trisaccharides. The core fucose-free trisaccharides are then elongated by glysocyltransferases to desired oligosaccharides, e.g., having sugar sequences identical to those found in naturally occurring human antibodies. Finally, the desired oligosaccharides are treated with β-1,4-galactosyltrasferase and α-2,6-siayltransferase sequentially to add galactose residues and then terminal sialic acid residues.

Example 4

Methods for Cleaving the Chitobiose Linkage of Fc N-Linked Glycans

Endo F2 and Endo F3 are unique in their ability to cleave complex structures. Endo F2 cleaves asparagine-linked or free oligomannose, and biantennary complex oligosaccharides. Oligomannose structures are cleaved at a 20-fold reduced rate. Fucosylation has little effect on Endo F2 cleavage of biantennary structures. It will not cleave hybrid structures. It cleaves between the two N-acetylglucosamine residues in the diacetylchitobiose core of the oligosaccharide, generating a truncated sugar molecule with one N-acetylglucosamine residue remaining on the asparagine.

Endo F3 is unique in that its cleavage is sensitive to the state of peptide linkage of the oligosaccharide, as well as the state of core fucosylation. Endoglycosidase F3 cleaves asparagine-linked biantennary and triantennary complex oligosaccharides. It will cleave non-fucosylated biantennary and triantennary structures at a slow rate, but only if peptide-linked. Core fucosylated biantennary structures are efficient substrates for Endo F3, even as free oligosaccharides. Endo F3 will also cleave fucosylated trimannosyl core structures on free and protein-linked oligosaccharides.

Figure 5:
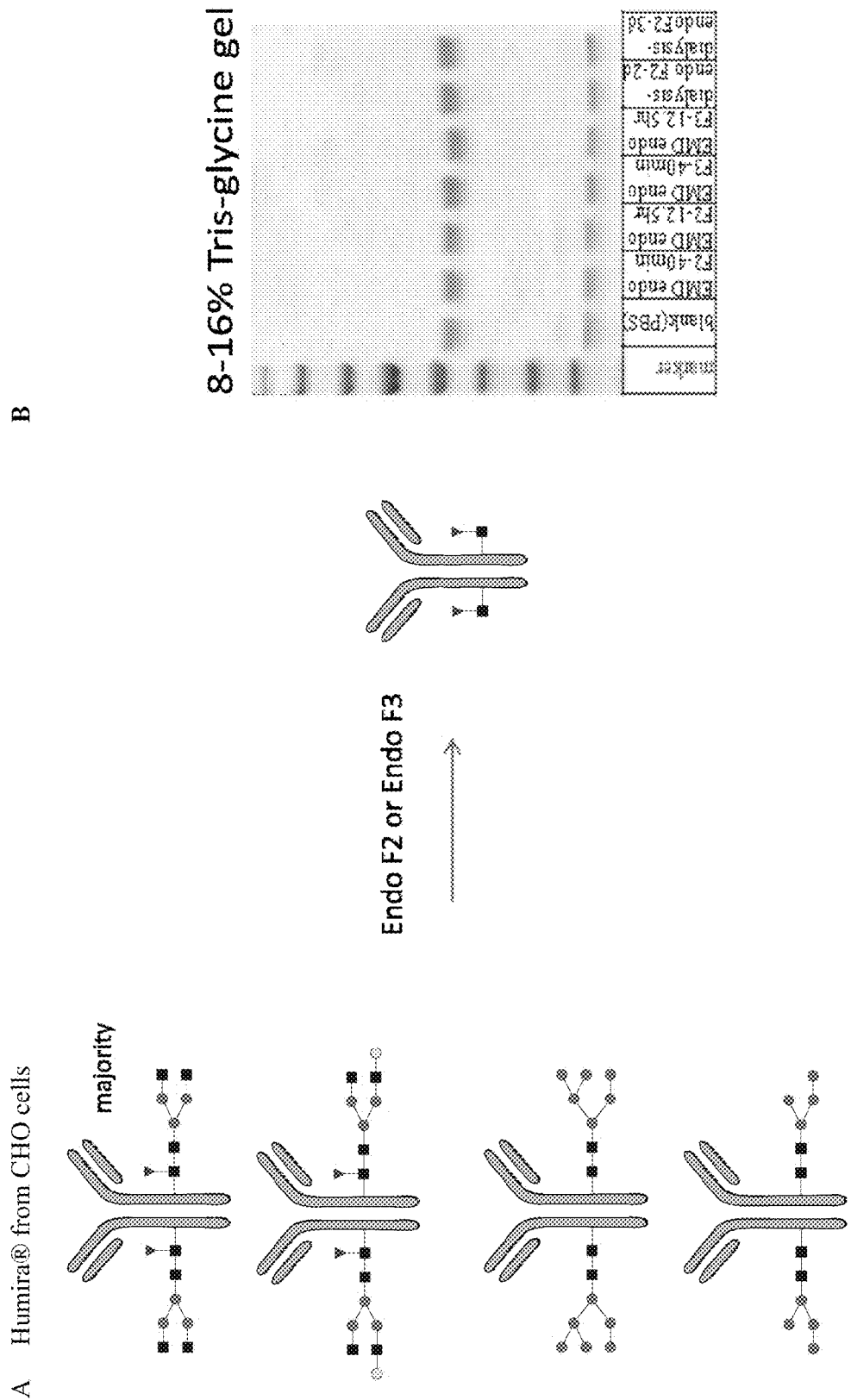
FIG. 5A shows a schematic illustration of digestion of heterogeneous glycoforms of Humira® obtained from Chinese hamster ovary (CHO) cells with Endo F2 and Endo F3. The results are shown in Coomassie stained polyacrylamide gels in FIG. 5B.

As shown in FIG. 5A, Humira® obtained from CHO cells, comprises a heterogeneous population of glycoforms with a predominance of the fucosylated glycoform (GlcNAc-Man)$_2$-Man-GlcNAc-GlcNAc(Fucose)-[Fc].

Digestion with Endo F2 (in 0.05M NaH$_2$PO$_4$, pH 4.54 buffer) or Endo F3 (in 0.05M CH$_3$COONa, pH 4.54 buffer) yielded a glycoform with a single fucosylated GlcNAc as visualized by 8-16% polyacrylamide gel electrophoresis in Tris-glycine buffer with Coomassie Blue stain (FIG. 5B)

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are encompassed within the scope of the claimed invention.

All publications and patent applications cited in this specification are herein incorporated by reference as if each individual publication or patent application were specifically and individually indicated to be incorporated by reference.

What is claimed is:

1. A method for glycan engineering the Fc region of a human, chimeric or humanized IgG1 or IgG3 glycosylated antibody, the method comprising the steps of:
    (a) providing a human, chimeric or humanized IgG1 or IgG3 glycosylated antibody comprising an oligosaccharide attached at each Asn 297 in the Fc region;
    (b) contacting the human, chimeric or humanized IgG1 or IgG3 glycosylated antibody with an endo-β-N-acetylglucosaminidase (endo-NAG) and alpha-fucosidase thereby digesting the oligosaccharide to a defucosylated N-Acetylglucosamine (GlcNAc) unit attached at each Asn 297 in the Fc region;
    (c) contacting the defucosylated N-Acetylglucosamine (GlcNAc) unit with an endo-β-N-acetylglucosaminidase (endo-NAG) and a synthetic Gal$_2$GlcNAc$_2$Man$_3$GlcNAc moiety joined to a leaving group, thereby coupling the terminal GlcNac of the synthetic Gal$_2$GlcNAc$_2$Man$_3$GlcNAc moiety to the defucosylated N-Acetylglucosamine (GlcNAc) unit to form the structure Gal$_2$GlcNAc$_2$Man$_3$GlcNAc$_2$ attached at each Asn 297 of the Fc region of the human, chimeric or humanized IgG1 or IgG3 glycosylated antibody; and
    (d) contacting the attached Gal$_2$GlcNAc$_2$Man$_3$GlcNAc$_2$ of step (c) with an alpha-2,6-sialyltransferase, CMP-Neu5Ac and a set of CMP-Neu5Ac regeneration enzymes comprising a pyrophosphatase and a cytidine monophosphate kinase, thereby adding a terminal Neu5Ac to each terminal galactose of the attached Gal$_2$GlcNAc$_2$Man$_3$GlcNAc$_2$, wherein the glycan engineered human, chimeric or humanized IgG1 or IgG3 antibody has a Neu5Ac$_2$Gal$_2$GlcNAc$_2$Man$_3$GlcNAc$_2$ attached at each Asn 297 in the Fc region, and wherein the CMP-Neu5Ac is regenerated following the addition of the terminal Neu5Ac.

2. The method of claim 1, wherein the leaving group is selected from the group consisting of: fluoride (F), OH (hydroxy), and oxazoline.

3. The method of claim 1, wherein the endo-β-N-acetylglucosaminidase (endo-NAG) in step (b) is selected from the group consisting of: Endo H, Endo A, Endo M, Endo F2, and Endo F3.

4. The method of claim 3, wherein the endo-β-N-acetylglucosaminidase (endo-NAG) used in step (b) is Endo H.

5. A method for glycan engineering the Fc region-of a human, chimeric or humanized IgG1 or IgG3 glycosylated antibody, the method comprising the steps of:
    (a) providing a human, chimeric or humanized IgG1 or IgG3 glycosylated antibody comprising an oligosaccharide attached at each Asn 297in the Fc region; and
    (b) contacting the human, chimeric or humanized IgG1 or IgG3 glycosylated antibody with an endo-β-N-acetylglucosaminidase (endo-NAG) and alpha-fucosidase thereby digesting the oligosaccharide to a defucosylated N-Acetylglucosamine (GlcNAc) unit attached at each Asn 297 in the Fc region; and;
    (c) contacting the defucosylated N-Acetylglucosamine (GlcNAc) unit with an endo-β-N-acetylglucosaminidase (endo-NAG) and a synthetic Neu5Ac$_2$Gal$_2$GlcNAc$_2$Man$_3$GlcNAc moiety joined to a leaving group, thereby coupling the terminal GlcNac of the synthetic moiety to the defucosylated N-Acetylglucosamine (GlcNAc) unit to form the structure $Neu5Ac_2Gal_2GlcNAc_2Man_3GlcNAc_2$ attached at each Asn 297 of the Fc region of the human, chimeric or humanized IgG1 or IgG3 glycosylated antibody.

6. The method of claim 5, wherein the leaving group is selected from the group consisting of: fluoride (F), OH (hydroxy), and oxazoline.

7. The method of claim 5, wherein the endo-β-N-acetyl-glucosaminidase (endo-NAG) in step (b) is selected from the group consisting of: Endo H, Endo A, Endo M, Endo F2, and Endo F3.

8. The method of claim 7, wherein the endo-β-N-acetyl-glucosaminidase (endo-NAG) used in step (b) is Endo H.

* * * * *